(12) United States Patent  (10) Patent No.: US 7,461,046 B2
Byington et al.  (45) Date of Patent: Dec. 2, 2008

(54) METHOD FOR CREATING AND USING A TREATMENT PROTOCOL

(75) Inventors: Carrie L. Byington, Salt Lake City, UT (US); Andrew T. Pavia, Salt Lake City, UT (US); John C. Christenson, Carmel, IN (US)

(73) Assignee: The University of Utah Research Foundation, Salt Lake City, UT (US)

( * ) Notice: Subject to any disclaimer, the term of this patent is extended or adjusted under 35 U.S.C. 154(b) by 212 days.

(21) Appl. No.: 10/503,033

(22) PCT Filed: Feb. 7, 2003

(86) PCT No.: PCT/US03/03789

§ 371 (c)(1),
(2), (4) Date: Jun. 7, 2005

(87) PCT Pub. No.: WO03/067399

PCT Pub. Date: Aug. 14, 2003

(65) Prior Publication Data

US 2006/0155663 A1  Jul. 13, 2006

(51) Int. Cl.
G06F 15/00 (2006.01)
G06F 15/18 (2006.01)
(52) U.S. Cl. .................................................. 706/62
(58) Field of Classification Search .................. 706/47
See application file for complete search history.

(56) References Cited

U.S. PATENT DOCUMENTS

| | | | | |
|---|---|---|---|---|
| 5,471,382 | A | * 11/1995 | Tallman et al. | 600/300 |
| 5,587,716 | A | 12/1996 | Sheynblat | |
| 5,660,176 | A | * 8/1997 | Iliff | 600/300 |
| 5,692,220 | A | 11/1997 | Diamond et al. | |
| 5,764,923 | A | * 6/1998 | Tallman et al. | 705/3 |
| 5,843,669 | A | * 12/1998 | Kaiser et al. | 435/6 |
| 5,964,700 | A | * 10/1999 | Tallman et al. | 600/300 |

(Continued)

OTHER PUBLICATIONS

A stochastic algorithm for risk assessment of in-stream contaminant Logan, L.; Ponnambalam, K.; Systems, Man and Cybernetics, 1998. 1998 IEEE International Conference on vol. 5, Oct. 11-14, 1998 pp. 4826-4831 vol. 5 Digital Object Identifier 10.1109/ICSMC.1998. 727616.*

(Continued)

Primary Examiner—Michael B Holmes
(74) Attorney, Agent, or Firm—Workman Nydegger

(57) ABSTRACT

Systems, devices, methods, and software are provided that are suitable for use in the creation, implementation, use and/or refinement of treatment protocols. The software is configured for use in a client-server environment where the server communicates with client devices such as PDAs, laptops, tablets, or desktop computers. The software is directed to programming for basing an assessment of risk of bacterial infection in a subject on the presence, or lack, of viral illness in that subject. The diagnosis of viral illness is made through the use of results obtained from an enterovirus polymerase chain reaction test or a direct fluorescent assay test for respiratory viruses. Such test data, in conjunction with 'time to positivity' data for urine, blood, cerebrospinal fluid, or other cultures, is then processed by the software to assess the individual risk of occurrence of various conditions, such as bacterial infection, in a particular subject.

59 Claims, 9 Drawing Sheets

U.S. PATENT DOCUMENTS

| | | | | |
|---|---|---|---|---|
| 6,117,674 | A * | 9/2000 | Goodwin et al. | 435/325 |
| 6,190,861 | B1 * | 2/2001 | Fishman | 435/5 |
| 6,194,149 | B1 * | 2/2001 | Neri et al. | 435/6 |
| 6,210,880 | B1 * | 4/2001 | Lyamichev et al. | 435/6 |
| 6,214,545 | B1 * | 4/2001 | Dong et al. | 435/6 |
| 6,235,494 | B1 * | 5/2001 | Hugli | 435/24 |
| 6,297,024 | B1 * | 10/2001 | Hugli et al. | 435/23 |
| 6,303,846 | B1 * | 10/2001 | Scelonge et al. | 800/279 |
| 6,355,437 | B1 * | 3/2002 | Neri et al. | 435/6 |
| 6,358,691 | B1 * | 3/2002 | Neri et al. | 435/6 |
| 6,368,788 | B1 * | 4/2002 | Kozhemyakin et al. | 435/5 |
| 6,372,424 | B1 * | 4/2002 | Brow et al. | 435/5 |
| 6,383,512 | B1 * | 5/2002 | Ciccarelli et al. | 424/450 |
| 6,468,982 | B1 * | 10/2002 | Weiner et al. | 514/44 |
| 6,537,558 | B2 * | 3/2003 | Kaniga | 424/234.1 |
| 6,559,294 | B1 * | 5/2003 | Griffais et al. | 536/23.1 |
| 6,579,696 | B1 * | 6/2003 | Shekhani et al. | 435/68.1 |
| 6,673,616 | B1 * | 1/2004 | Dahlberg et al. | 436/6 |
| 6,680,169 | B2 * | 1/2004 | Morrow et al. | 435/5 |
| 6,699,663 | B1 * | 3/2004 | Fishman | 435/6 |
| 6,709,815 | B1 * | 3/2004 | Dong et al. | 435/6 |
| 6,709,819 | B2 * | 3/2004 | Lyamichev et al. | 435/6 |
| 6,777,195 | B2 * | 8/2004 | Kozhemyakin et al. | 435/7.24 |
| 6,780,585 | B1 * | 8/2004 | Dong et al. | 435/6 |
| 6,799,122 | B2 * | 9/2004 | Benson | 702/20 |
| 6,858,391 | B2 * | 2/2005 | Nunez et al. | 435/6 |
| 6,865,926 | B2 * | 3/2005 | O'Brien et al. | 73/23.27 |
| 6,875,585 | B2 * | 4/2005 | Bech-Jansen | 435/69.1 |
| 6,899,880 | B2 * | 5/2005 | Stephens et al. | 424/190.1 |
| 6,905,816 | B2 * | 6/2005 | Jacobs et al. | 435/5 |
| 6,951,721 | B2 * | 10/2005 | Murphy | 435/6 |
| 6,952,945 | B2 * | 10/2005 | O'Brien | 73/23.35 |
| 6,965,023 | B2 * | 11/2005 | Reed et al. | 536/23.5 |
| 7,001,759 | B1 * | 2/2006 | Weiner et al. | 435/320.1 |
| 7,033,781 | B1 * | 4/2006 | Short | 435/69.1 |
| 7,041,490 | B1 * | 5/2006 | Griffais et al. | 435/252.3 |
| 7,041,491 | B2 * | 5/2006 | Inohara et al. | 435/253.3 |
| 7,060,436 | B2 * | 6/2006 | Lyamichev et al. | 435/6 |
| 7,060,442 | B2 * | 6/2006 | Nunez et al. | 435/6 |
| 7,060,479 | B2 * | 6/2006 | Dumas Milne Edwards et al. | 435/196 |
| 7,067,643 | B2 * | 6/2006 | Dahlberg et al. | 536/23.1 |
| 7,083,957 | B2 * | 8/2006 | Rosenblum et al. | 435/183 |
| 7,087,381 | B2 * | 8/2006 | Dahlberg et al. | 435/6 |
| 7,101,672 | B2 * | 9/2006 | Dong et al. | 435/6 |
| 7,101,963 | B2 * | 9/2006 | Griffais et al. | 530/300 |
| 7,136,694 | B2 * | 11/2006 | Hadley et al. | 600/515 |
| 7,167,744 | B2 * | 1/2007 | Hadley et al. | 600/515 |
| 7,167,745 | B2 * | 1/2007 | Hadley et al. | 600/515 |
| 7,174,204 | B2 * | 2/2007 | Hadley et al. | 600/515 |
| 7,187,790 | B2 * | 3/2007 | Sabol et al. | 382/128 |
| 7,202,227 | B2 * | 4/2007 | Boutin | 514/44 |
| 7,208,274 | B2 * | 4/2007 | Dhallan | 435/6 |
| 7,220,728 | B2 * | 5/2007 | Weiner et al. | 514/44 |
| 7,257,987 | B2 * | 8/2007 | O'Brien et al. | 73/23.41 |
| 7,311,839 | B2 * | 12/2007 | Schulze-Makuch et al. | 210/660 |
| 7,322,369 | B2 * | 1/2008 | Medina | 134/25.3 |
| 7,404,931 | B2 * | 7/2008 | Frey et al. | 422/101 |
| 2002/0004729 | A1 | 1/2002 | Quattrocchi et al. | |
| 2003/0138819 | A1 | 7/2003 | Gong et al. | |

OTHER PUBLICATIONS

Infectious disease and climate change: detecting contributing factors and predicting future outbreaksAndrick, B.; Clark, B.; Nygaard, K.; Logar, A.; Penaloza, M.; Welch, R.; Geoscience and Remote Sensing, 1997. IGARSS '97. 'Remote Sensing—A Scientific Vision for Sustainable Development'., 1997 IEEE International vol. 4, Aug. 3-8, 1997.*

A stochastic algorthm for risk assessment of in-stream contaminant Logan, L.; Ponnambalam, K.; Systems, Man, and Cybernetics, 1998. 1998 IEEE International Conference on vol. 5, Oct. 11-14, 1998 pp. 4826-4831 vol. 5 Digital Object Identifier 10.1109/ICSMC.1998.727616.*

Infectious disease and climate change: detecting contributing factors and predicting future outbreaksAndrick, B.; Clark, B.; Nygaard, K.; Logar, A.; Penaloza, M.; Welch, R.; Geoscience and Remote Sensing, 1997. IGARSS '97. 'Remote Sensing—A Scientific Vision for Sustainable Development'., 1997 IEEE International vol. 4, Aug. 3-8, 1997 Page(s).*

Scully et al. Case 25-2001 of the New England Journal of Medicine, vol. 345, No. 7, Aug. 16, pp. 256-532.*

Estimation of bone mineral density data using MoG neural networks Rizzi, A.; Panella, M.; Paschero, M.; F.M.F.; Neural Networks, 2004. Proceedings. 2004 IEEE International Joint Conference on vol. 4, 25-29 Jul. 2004 pp.:3241-3246 vol.4.*

Identification of dental bacteria using statistical and neural approaches Chaw Koh Yong: Choo Min Lim; Plumbley, M.; Beighton, D.; Davidson, R.; Neural Information Processing, 2002. ICONIP '02. Proceedings of the 9th International Conference on vol. 2, Nov. 18-22, 2002 pp.:606 - 610 vol.2 Digital object Identifier 10.1109/ICONIP.2002.1198129.*

P3D-2 ROC Analysis of Ultrasound Elasticity Imaging of Breast Abnormalities Burnside, E.S.; Hall, T.J.; Sommer, A.M.; Sisney, G.A.; Hesley, G.K.; Hangiandreou, N.J.; Svensson, W.E.; Ultrasonics Symposium, 2006. IEEE Oct. 2-6, 2006 pp.:2048 - 2051 Digital Object Identifier 10.1109/ULTSYM.2006.522.*

Mani S. et al.: "Guideline generation from data by induction of decision tables using a Bayesian network framework." Proceedings/ AMIA . . . Annual Symposium. AMIA Symposium 1998, 1998, pp. 518-522.

Buntine W.: "A guide to the literature on learning probabilistic networks from data." IEEE Transactions on Knowledge and Data Engineering, IEEE Service Center, Los Alamitos, CA, US, vol. 8, No. 2, Apr. 1996, pp. 195-210.

Buntine W.: "Learning classification trees." Statistics and Computing, London, GB, vol. 2. No. 2, Jun. 1993, pp. 63-73.

Pearl J.: "Probabilistic reasoning in intelligent systems: networks of plausible inference." Sep. 1998, Morgan-Kaufmann, ISBN 1-55860-479-0, Chapter 8: Learning structure from data (p. 381-408).

Supplementary Partial European Search Report, EP 03 71 3398, Feb. 2, 2007.

* cited by examiner

METHOD FOR CREATING AND USING A TREATMENT PROTOCOL

BACKGROUND OF THE INVENTION

1. Field of the Invention

The present invention relates generally to treatment protocols. More particularly, embodiments of the present invention relate to systems, devices, methods, and software for use in the creation, implementation, use and/or refinement of treatment protocols.

2. Related Technology

Young infants are particularly susceptible to a wide variety of infections, diseases and conditions. While some of these infections, diseases and conditions may be relatively benign, others can pose a significant threat to the health and well being of the infant. Bacterial infections, for example, are of particular concern because they can cause potentially life-threatening fever in very young infants. Accordingly, even though the risk of occurrence of a bacterial infection, for example, may be relatively low, typical treatment protocols tend to favor admission of the infant to the hospital for treatment of the infection with an aggressive antibiotic therapy. While, as discussed below, such treatment can be problematic, the treating physician, generally not a pediatric specialist, often tends to view any disadvantages as being acceptable in light of the potential risk to the life of the child if a less aggressive approach to treatment is taken.

As suggested above, protocols have been developed concerning the treatment of febrile infants. One commonly employed treatment protocol is sometimes referred to as the 'Rochester criteria.' The Rochester criteria were developed in 1985 with a view towards classifying infants with fever, according to the risk that such infants had a bacteria-induced fever. As disclosed elsewhere herein, the Rochester criteria are generally concerned with: (i) selected aspects of the medical history of the infant; (ii) results of a physical examination of the infant; and (iii) a laboratory evaluation of, for example, the urine and blood of the infant.

Application of the Rochester criteria to a particular infant produces a risk profile for the infant. Once classified according to level of risk, the infants could be treated accordingly. By way of example, if an infant satisfactorily fulfills all of the Rochester criteria, that infant would be classified as being at 'low risk' for contracting a serious bacterial infection ("SBI"). On the other hand, if an infant were under ninety (90) days of age, had a fever of 38° C. or higher, and missed any one of the fifteen (15) Rochester criteria, that infant would likely be classified as being 'high risk,' with a risk of having a serious bacterial infection of about twenty one percent (21%). Infants falling into the 'high risk' category are generally admitted to the hospital and treated as described above. Such admission and treatment is sometimes referred to as a 'rule out sepsis' ("ROS") evaluation.

Notwithstanding the benefits that may be realized by the 'fail safe' approach implicated by the Rochester criteria and similar protocols, this type of approach to treatment of the young febrile infant has proven to be problematic. By way of example, parents can become traumatized when informed that an ROS evaluation is required because their child may have a life-threatening illness. In this regard, there is often a significant, adverse psychological effect on the parent, sometimes referred to as 'the vulnerable child syndrome,' where parents tend to treat such infants differently is because it is the perception of the parents that the child is weak or sickly. Moreover, a stay in the hospital is traumatic for the infant as well as for the parents. By way of example, trauma to the infant may occur when breast feeding of the infant is interrupted for the performance of various procedures or the administration of drugs or antibiotics. Further, infections and other complications may also occur as a result of hospitalization of the infant.

Not only does the use of the Rochester criteria, and similar approaches, implicate various concerns for both the parent and the infant with respect to the ROS evaluation, but questions now exist as to the usefulness of the Rochester criteria, at least when it is employed as the sole basis for admission and ROS evaluation decisions. By way of example, more recent studies have shown that a febrile infant less than ninety (90) days old with a 38° C. degree temperature, that misses one of the Rochester criteria, has a risk of having a bacterial infection of only about nine percent (9%), in contrast with the twenty one percent (21%) figure reported when the Rochester criteria were initially developed. Thus, the ability of the Rochester criteria to accurately predict bacterial infections and, thus, the usefulness of the Rochester criteria, has diminished considerably over time.

The diminished utility of the Rochester criteria is due in part to the occurrence of various changes that have influenced the epidemiology of bacterial infection in infants. Examples of such changes include: (i) universal immunization against *Haemophilus influenzae*; routine screening and intrapartum antibiotic prophylaxis for the prevention of group B *Streptococcus* infection; and (iii) the introduction of immunization against *Streptococcus pneumoniae*. Thus, while such changes have dramatically reduced the incidence of disease due to these pathogens, little or no reassessment has been made of the risk of bacterial infection in the febrile infant. Not only has the usefulness of the Rochester criteria diminished with the passage of time, but the underlying approach exemplified by the Rochester criteria is cause for concern as well. In particular, the Rochester criteria and other similar schemes are designed to identify only those infants at risk for bacterial infection However, studies have shown that only about eight infants out of a hundred typically contract a bacterial infection. Moreover, some studies have shown that while fever in young infants does occur as a result of bacterial pathogens, it is much more likely that a fever in a young infant is due to a benign viral illness. Treatment of a viral illness with antibiotics, such as would be dictated by the Rochester criteria, is thus ineffective, time-consuming and expensive.

Although a significant majority of fevers in young infants are due to viral pathogens, the use of treatment protocols such as those implicated by the Rochester criteria nonetheless persist. The rationale for the persistence of the use of such treatment protocols relates, at least in part, to the identification of viral and bacterial pathogens in young infants.

By way of example, there is presently no known reliable method for rapidly and reliably detecting and identifying bacterial infections in young infants. Moreover, only limited information has been available concerning testing for viral pathogens, and the management of infants with viral infections. In light of the foregoing, it is generally considered a prudent course of action to presume that any fever presented in a young infant is due to bacterial pathogens, and to admit the infant for treatment with a corresponding course of antibiotics.

As suggested by the foregoing, the Rochester criteria and similar treatment protocols tend to result in the over-prescription of antibiotics for febrile infants, notwithstanding that a significant majority of the fevers presented in young infants are a result of benign viral illness. Such a result is problematic because over-prescription of antibiotics, also referred to as 'antimicrobials,' is a factor that contributes to increased antimicrobial resistance among bacterial pathogens such as are commonly encountered in pediatrics. This increase in antimicrobial resistance tends to diminish the effectiveness of many known antibiotics in treating fevers and other conditions that result from bacterial pathogens. Additionally, certain antimicrobials contribute to secondary diseases directly caused by the agents themselves.

In view of the foregoing problems, and other problems in the art not specifically enumerated herein, what is needed are systems, devices, methods, and software for use in the creation, implementation, use and/or refinement of various treatment protocols. Implementations of the systems, methods and/or software should be configured for use in connection with a variety of different types of computing environments.

Among other things, such systems, devices, methods, and software should identify relationships implicit or explicit in bodies of patient data, and should advantageously implement such relationships, either alone or in connection with established protocols, in the form of rule-based treatment protocols that permit rapid and accurate assessments of, for example, the risk of serious pathologic infection in a patient. At least some of such protocols should be based at least in part upon information and data concerning both bacterial and viral epidemiology and testing.

Furthermore, the systems, devices, methods, and software should permit periodic reassessment of data in order to facilitate refinement of existing treatment protocols and/or the development of new treatment protocols. Finally, the systems, methods and software should be configured to operate in various modes, including a real time mode, and should implement various management functionalities such as the definition and printing of various types of reports.

BRIEF SUMMARY OF AN EXEMPLARY EMBODIMENT OF THE INVENTION

In general, embodiments of the invention relate to systems, devices, methods, and software for use in the creation, implementation and use of various treatment protocols.

An exemplary implementation of the invention is embodied as software configured for use in a client-server environment where the server is configured for communication with a plurality of client devices such as PDAs, laptops, tablets, or desktop computers. The software includes programming for assessment of risk of bacterial infection in a subject on the presence, or lack, of viral illness in that subject.

Exemplary, the diagnosis of viral illness is made through the use of results obtained from an enterovirus polymerase chain reaction ("EV PCR") test or a direct fluorescent assay ("DFA") test for respiratory viruses. Such test data, in conjunction with 'time to positivity' data for urine, blood, cerebrospinal fluid ("CSF"), or other cultures, is then processed by the software to assess the individual risk of occurrence of various conditions, associated with pathogens, in a particular subject.

In operation, bacterial and viral data is entered into the program, either automatically by the testing device(s), or manually. The software then processes and analyzes the data, either on an ad hoc or periodic basis, to assess the risk of the occurrence of a predefined condition in the patient. Once the risk is determined, the treating physician can decide upon a course of action to take with respect to the patient. Exemplary, the risk assessment can be performed as soon as the patient is evaluated and can be updated as test results become available, or at regularly scheduled intervals such as 4, 8, 12, 16, and 24 hours.

In this way, the treating physician can quickly and reliably determine whether a viral or bacterial infection is present, and take appropriate action. When employed in this context, the software contributes to a reduction in ROS evaluations and, thus, a decrease in hospital admissions and corresponding reduction in treatment costs. In connection with the foregoing, the software also helps to limit antibiotic prescription to those cases where a bacterial infection is determined to be present.

These and other aspects of embodiments of the present invention will become more fully apparent from the following description and appended claims.

BRIEF DESCRIPTION OF THE DRAWINGS

In order that the manner in which the above-recited, and other aspects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF SELECTED EMBODIMENTS OF THE INVENTION

Reference will now be made to the drawings to describe various exemplary embodiments of the invention. It is to be understood that the drawings are diagrammatic and schematic representations of such exemplary embodiments, and are not limiting of the scope of the present invention in any way, nor are they necessarily drawn to scale.

The present invention relates generally to systems, devices, methods, and software for use in the creation, implementation and use of various treatment protocols. As described below, embodiments of the invention facilitate, among other things, the empirical identification of various relationships present in, or otherwise implicated by, various data of interest. Further, exemplary embodiments of the invention are configured to implement such relationships, either alone or in connection with established protocols, in the form of rule-based treatment protocols that permit rapid and accurate assessments of, for example, the risk of serious pathologic infection in a patient. Moreover, exemplary protocols employ information and data concerning both bacterial and viral epidemiology and testing. Additionally, by providing accurate and rapid results, as in the case of viral and bacterial infection diagnoses for example, embodiments of the invention aid in reducing the over-prescription of antibiotics, thereby aiding in the preservation of the effectiveness of such antibiotics by limiting exposure of bacterial pathogens to antibiotics only when necessary. In connection with the foregoing, exemplary embodiments of the invention also serve to decrease the number of unnecessary testing and admissions, thereby reducing costs.

I. Aspects of an Exemplary Operating System

Figure 1:
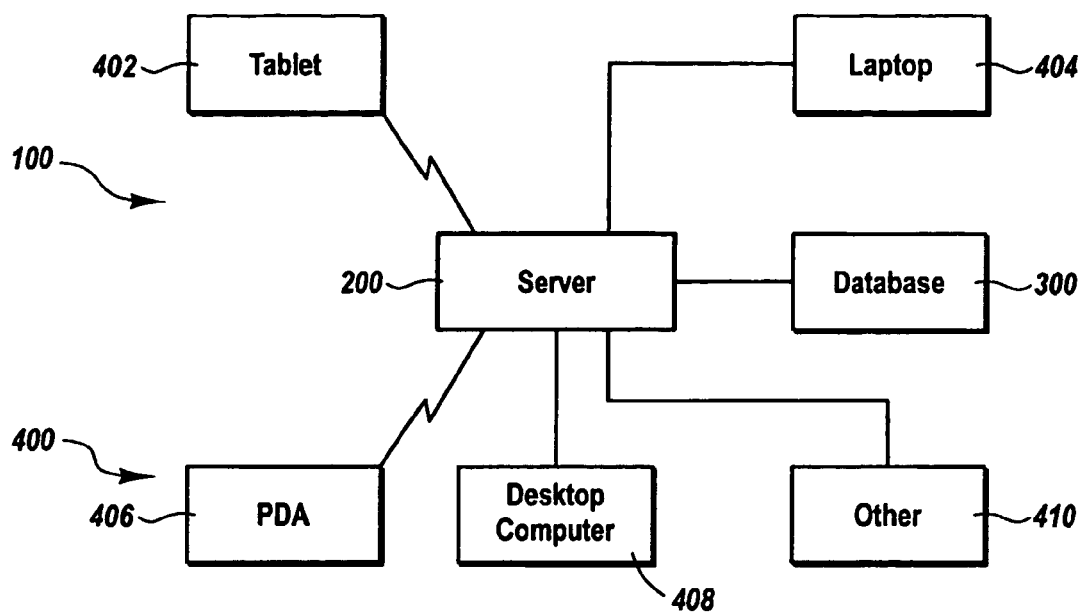
FIG. 1 is a block diagram that illustrates general aspects of an exemplary operating environment for some embodiments of the invention.

With attention now to FIG. 1, details are provided concerning various aspects of an exemplary operating environment in connection with which some embodiments of the invention may be implemented. As indicated there, an operating environment 100 is provided that is generally configured in the form of a client-server arrangement. More particularly, the operating environment 100 includes a server 200 in communication with a database 300. In some implementations, the server 200 and database 300 are co-located. However, the server 200 and database 300 may reside in different locations. Moreover, the server 200 and database 300 may be co-located with various client devices 400. Alternatively, the server 200 and/or database 300 may be disposed in locations that are geographically remote from the client devices 400.

More generally however, any arrangement of the server 200, the database 300 and the client devices 400 may be employed that is effective in implementing aspects of the functionality disclosed herein. Accordingly, the scope of the invention should not be construed to be limited to any particular implementation or arrangement of the operating environment 100 and its associated elements and components. Further details concerning various exemplary operating environments for implementations of the invention are provided elsewhere herein.

As noted above, the exemplary operating environment 100 includes a variety of client devices 400 configured for hardwire and/or wireless based communications with the server 200. Exemplary client devices 400 include, but are not limited to, electronic tablets 402, laptop computers 404, personal data assistants ("PDA"s) 406, desktop computers 408, and various other client devices 410. It should be noted that the illustrated combination of client devices 400 is exemplary only and is not intended to limit the scope of the invention in any way.

One aspect of the exemplary operating environment 100 illustrated in FIG. 1 is that one or more of the various client devices 400 are able to achieve real-time, high speed communications with the server 200 and database 300. A related aspect of the operating environment 100 is that, as a result of its central location, the server 200, in cooperation with the database 300, is able to rapidly assimilate and process data received from one or more of the client devices 400. Similarly, in the event that is desired to populate one or more of the client devices 400 with some or all of the data contained in the database 300, the server 200 is able to quickly and reliably synchronize the data on or more of the client devices 400, substantially simultaneously. In this way, the users of the client devices 400 can be assured that at any given time, the data that they possess and/or to which they have access, is the most current data available.

II. Exemplary Systems and Methods for Protocol and Rule Development

Figure 2:
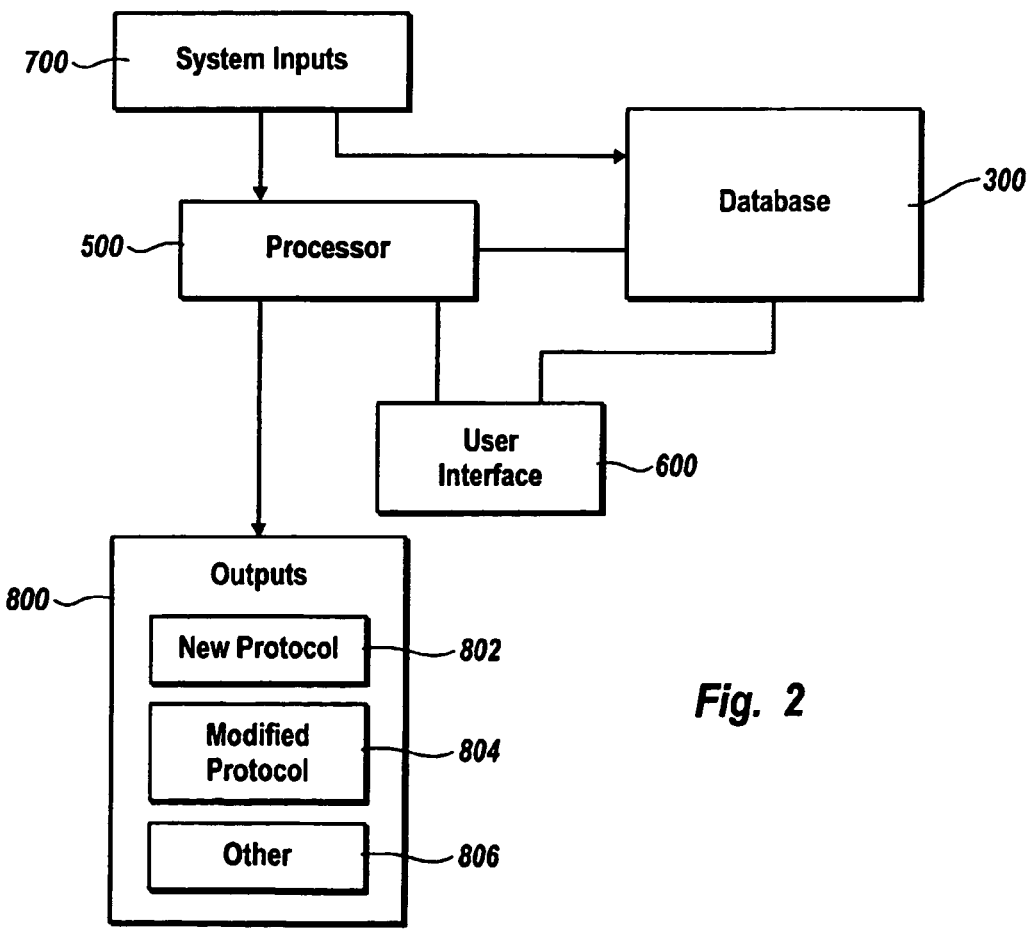
FIG. 2 is a block diagram that illustrates aspects of an exemplary system as may be employed in the development and/or refinement of treatment protocols.

Directing attention now to FIG. 2, details are provided concerning various elements of a system that may be used to develop and/or refine treatment protocols and other materials. In at least some cases, the treatment protocol is comprised of, among other things, data and information, as well as rules of various types, so that development and/or refinement of a protocol may implicate, among other things, the development and refinement of various rules associated with the protocol, as well as the addition and/or removal of various rules to/from the particular protocol. More generally, a treatment protocol may comprise any combination of rules, information, data, and/or any other materials useful in the diagnosis and/or treatment of various conditions.

Further, at least some embodiments of the invention are concerned with the development and/or use of a treatment protocols which may be designed based upon a body of data having certain predefined characteristics. More specifically, some embodiments of the invention are concerned with the use of viral infection test results, such as may be obtained from, for example, an enterovirus polymerase chain reaction ("EV PCR") test or a direct fluorescent assay ("DFA") test for respiratory viruses.

Such tests, or others of comparable functionality, are employed in conjunction with 'time to positivity' data for urine, blood, cerebrospinal fluid ("CSF"), or other cultures, to assess the individual risk of occurrence of various conditions, such as bacterial infection, in a particular subject.

As discussed in further detail below, some embodiments of the invention thus allow a user to predict or assess, based on the presence of a viral illness, what the risk is of that same subject having a concomitant bacterial illness. As noted earlier, this is a useful feature at least because it is known that bacterial illness is presently the most serious cause of febrile episodes. Thus, the ability to predict bacterial illness translates closely to an ability to predict outcomes of febrile episodes.

Moreover, because viral illnesses occur during various seasons, the presence of a particular type of virus can be used as an aid to predict the likelihood of a concomitant bacterial illness. As discussed in further detail herein, this feature of the invention, used in conjunction with "time to positivity" for various bacterial cultures, permits reliable assessments to be quickly made as to the risk that a bacterial illness, and fever, will occur in a given subject in a given period of time.

In addition to facilitating development of treatment protocols, systems and methods such as those exemplary embodiments depicted in FIGS. 2 and 3 (discussed below), respectively, may also be used in the development of various tools, such as the risk assessment module of FIG. 4 (discussed below), that may be used to aid in the implementation of one or more aspects of a treatment protocol.

Referring generally now to FIG. 2, the database 300 is employed in connection with a processor 500 and user interface 600. The processor 500 may, in some implementations, comprise an element of server 200. Alternatively, the processor 500 and user interface 600 may comprise elements of a computing device distinct from the server 200. Moreover, one or more of the database 300, the processor 500, and the user interface 600 may be co-located with another component or, alternatively, may be located at geographically diverse locations.

In yet other exemplary implementations, the user interface 600 comprises an element of one or more of the client devices 400. As suggested by the foregoing, the development, assessment and refinement of various rules and treatment protocols may be implemented, or otherwise facilitated, through the use of a variety of hardware and software configurations and, accordingly, the scope of the invention should not be construed to be limited to any particular configuration or implementation. More generally, any combination of hardware and software effective in implementing aspects of the functionality disclosed herein may be employed.

In general, and as suggested in FIG. 2 the processor 500 is programmed to receive various system inputs 700 that may, for example, be specified and entered by way of user interface 600. Generally, the system inputs 700 are received and processed by the risk assessment module 1000. Further, the database 300 exemplarily includes information and data concerning various diagnostic and treatment actions so that the output of the risk assessment module can be correlated with one or more particular actions that can then be presented or recommended to the treating physician.

Some examples of system inputs 700 that may be used in connection with the development, refinement and/or implementation of various treatment protocols are considered below in the discussion of FIGS. 4 through 8. The various programming instructions associated with the processor 500 operate to permit the manipulation, such as by performance of various statistical analyses, of the system input 700 so as to facilitate the development of various outputs 800.

As exemplified in FIG. 2, the outputs 800 that may be produced include, but are not limited to, new treatment protocols 802, modified treatment protocols 804, as well as various other materials 806, such as rules suitable for use in connection with the definition or implementation of treatment protocols. It should be noted that various additional, or alternative, components may be employed in connection with the development of materials such as new protocols 802 and modified protocols 804. Accordingly, the scope of the invention should not be construed to be limited to the exemplary implementation illustrated in FIG. 2.

Figure 3:
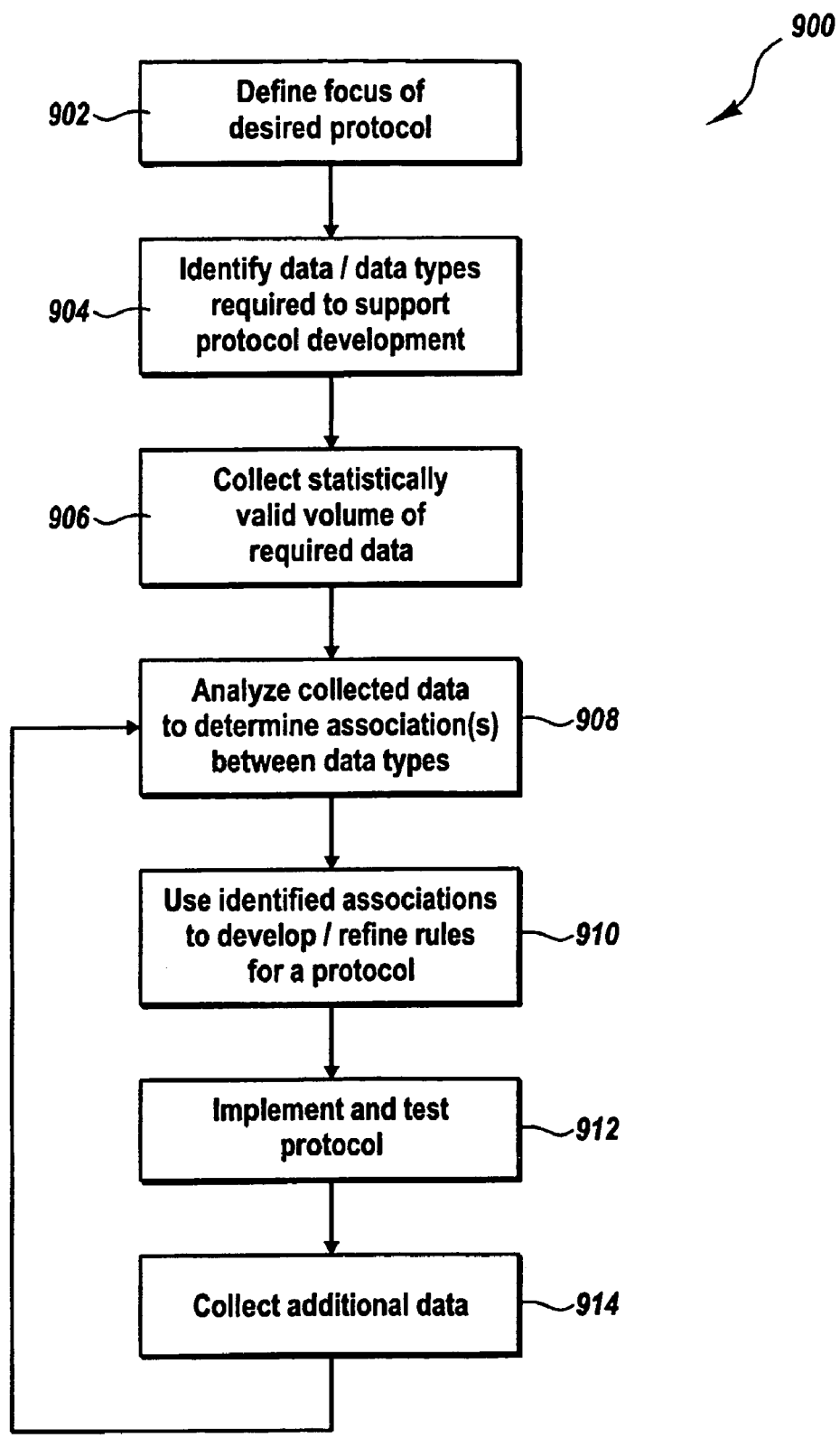
FIG. 3 is a flow chart that illustrates various stages of an exemplary process by which a treatment protocol may be developed and refined.

Turning now to FIG. 3, aspects of an exemplary process 900 that may be employed, in connection with a system such as that depicted in FIG. 2, to facilitate development and/or refinement of a treatment protocol are illustrated. At the initial stage 902 of the process 900, the focus or subject matter of the desired protocol is defined. Generally, the subject matter of a particular protocol that is desired to be developed may relate to any area of medical diagnosis or treatment that may be of interest. One example of such subject matter concerns the diagnosis and treatment of the young febrile infant, as discussed in further detail below.

The definition of the subject matter or focus of a particular protocol may be implemented in any of a variety of ways. By way of example, a particular protocol, rules, and other materials may be defined or constructed with reference to various known information such as, but not limited to, clinical studies, test data, and epidemiological information. However, any other information, data or materials suitable for use in connection with the solution of the problem or problems to which the desired protocol is to be directed may likewise be employed.

Once the focus or subject matter of the desired protocol has been defined, the process 900 moves to stage 904. At stage 904, identification is made of the various data and data types, and/or other materials, anticipated to be required to support development of the desired protocol. It should be noted that various exemplary data types are discussed below in connection with FIGS. 4 through 8. Various other data and data types may likewise be employed however. In at least some cases, refinement of an existing protocol may include, among other things, selection of additional or alternative data and data types. Thus, the nature of the protocol is not static in every case and, instead, may be dynamic so as to allow protocol changes as new information, data and other materials are developed.

At such time as a determination has been made as to the data and data types required to support protocol development, the process 900 advances to stage 906 where a body of data is collected that is of sufficient size and scope to provide statistically valid results. As discussed in further detail below, embodiments of the invention are suitable for use in connection with situations where the body of data upon which the protocols are based is dynamic and varies with time. After a sufficiently large body of data has been collected, the process 900 then moves to stage 908.

In general, stage 908 is concerned with the analysis and processing of the collected data in order to determine, empirically in at least some instances, and describe various associations that may exist or be established between the various data types. In at least some implementations of the invention, the analysis performed at stage 908 comprises various types of statistical analyses.

By way of example, some implementations of the invention employ a Bayesian approach to the identification and description of associations between various data types. In some cases, for example, a Bayesian approach will result in the classification of various data or data types as independent variables on one hand, and dependent variables on the other hand, where one or more of the dependent variables are expressed as some function of one or more of the independent variables. Thus, this type of analytical approach is useful in identifying and describing relationships between the collected data and data types that may not otherwise be readily apparent. It should be noted in connection with the foregoing that the use of Bayesian analytic techniques in connection with the development of various treatment protocols, rules and other materials is exemplary only and, more generally, various other statistical analyses and other analytical techniques may likewise be employed. For example, other statistical analyses that may prove useful in connection with the development of treatment protocols include, but are not limited to, ×2 analyses and multiple logistical regression.

At such time as one or more associations are identified between various aspects of the collected data, the process 900 moves to stage 910 where the identified associations are used to develop and/or refine rules suitable for use in the creation of one or more treatment protocols. One example of this, discussed in further detail below, concerns the use of Bayesian modeling in the treatment of young febrile infants. In this example, a Bayesian modeling process directed to various patient data gathered over a period of time reveals that infants with a viral illness only rarely contract a concomitant bacterial infection. A rule is thus developed that indicates that young febrile infants with viral illnesses can be released from a hospital rather than being treated with antibiotics for a bacterial infection that was not present and unlikely to occur.

The foregoing is but one example of the way in which the functionality implicated at stage 910 can be implemented and, accordingly, the scope of the invention should not be construed to be so limited. At such time as one or more treatment protocols have been defined and developed, stage 912 of the process is entered where the protocol is implemented and tested for suitability in terms of such factors as validity, safety, accuracy and usefulness.

In at least some implementation of the invention, the rules and protocols initially developed can be reexamined and refined on a periodic or other basis, based upon factors such as changes to the database in connection with which the protocols were initially developed. Thus, as indicated in FIG. 3, subsequent to the implementation and testing of the protocol, or simultaneously therewith, the process 900 advances to stage 914 where additional data is collected and added to the database. The process then returns to stage 908 where the new data and old data are collectively analyzed to determine and/or verify, as applicable, various associations between data types or other aspects of the collected data. The process 900 then continues as before.

As suggested by the foregoing, one aspect of this implementation of the invention is that users are able to take advantage of the experiences and findings of other users so that the protocols can be continuously updated and refined to account for the various factors that may affect in some way the data that is entered into the database. In this way, changes to the protocols may be implemented in a substantially smooth and continuous manner, rather than as a series of widely spaced significant changes that may disrupt patient care or other factors to which the treatment protocols relate. Moreover, the various refinements to the protocols can be stored as revisions to the initially developed protocol so that trend analyses and other processes may be performed to identify changes to the protocols that have occurred over a period of time.

As discussed above, one aspect of the embodiments of the invention is that various tools can be developed for use in connection with the provision of medical treatment. With particular attention now to FIG. 4, details are provided concerning software, exemplarily implemented as a risk assessment module 1000 that can be run from server 200, for example. In general, the risk assessment module 1000 is configured to employ various system inputs 700 in the development of an assessment of the risk that a young febrile infant will develop a serious bacterial infection.

As noted earlier however, the tool illustrated in FIG. 4 is exemplary only and its not intended to limited the scope of the invention in any way. More generally, any of a variety of tools and/or protocols may be developed and used consistent with the invention, and such tools and protocols are not limited to any particular area of endeavor in the medical field.

Figure 4:
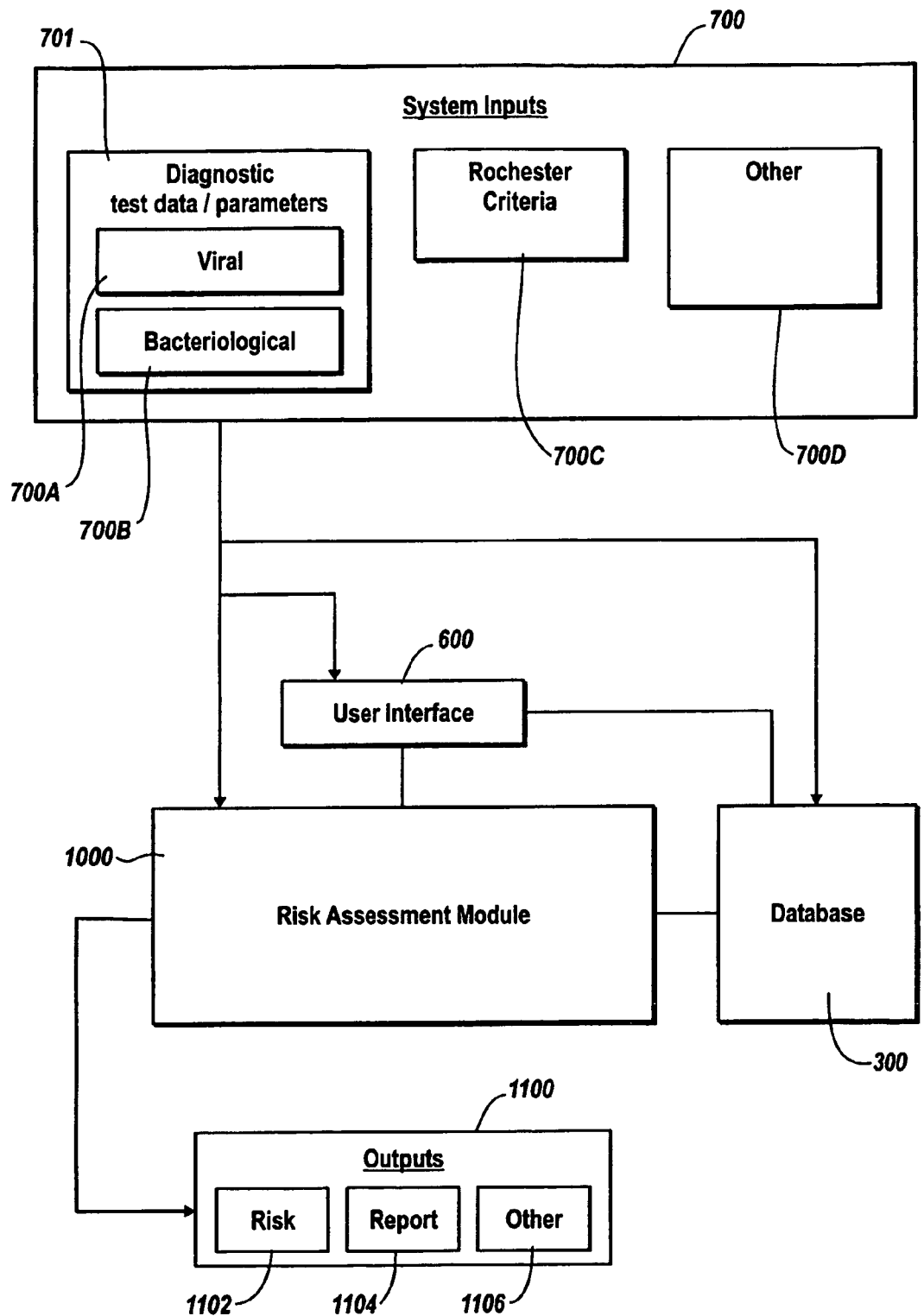
FIG. 4 is a block diagram that illustrates a system for generating risk assessments, reports and other materials based on various system inputs.

With continuing attention now to FIG. 4, the risk assessment module 1000 is configured for communication with the user interface 600 and a database 300 and receives various system inputs 700 which are then processed and used to develop various outputs 1100. As noted above in connection with the discussion of FIG. 1, the server 200, database 300, and user interface 600, may be configured for real-time communication with the client devices 400, and/or other, client devices, databases, servers, or networks. In this way, the system inputs 700 can be analyzed, uploaded, downloaded, or otherwise processed, in real time. Moreover, the processes implemented by way of, or in connection with, the risk assessment module 1000 can be performed on any temporal basis, such as intermittently, periodically, automatically, ad hoc, or otherwise.

One aspect of a real time communication implementation is that a particular risk, such as that any given subject will develop a bacterial illness, can be reevaluated at any time the user desires. As is the case with many tools that employ statistical analyses, the results obtained with embodiments of the present invention improve over time as the body of data upon which the analyses are based grows in size.

In this exemplary implementation, the system inputs 700 include various viral and bacteriological diagnostic test data and parameters 701, discussed in further detail below, as well as Rochester criteria 700C, and various other factors 700D. Further details concerning the viral and bacteriological diagnostic test data and parameters 701, the Rochester criteria 700C, and the other factors 700D are provided below in connection with the discussion of FIGS. 5 through 8. As suggested in FIG. 4, some or all of the system inputs 700 may be entered or made accessible to the risk assessment module 1000 directly from test equipment, for example, and/or by way of the user interface 600. Additionally, some implementations provide for entering system inputs 700 into the database 300. Various other arrangements may likewise be employed however.

With regard to data storage and usage, the structure and contents of the database(s) 300 and/or associated data structures can be customized or constructed in various ways to include particular sets or combinations of system inputs. In this way, analyses performed by the risk assessment module 1000 can be narrowly tailored to suit particular groups of patients, circumstances and/or other considerations. Consequently, embodiments of the invention can be customized as necessary for employment in a wide range of circumstances and situations.

As suggested by the foregoing, one aspect of the risk assessment module 1000 is that it is able to integrate research findings, diagnostic tests and patient-specific test results, collectively denoted as the system inputs 700, in order to generate risk assessments, reports and various other outputs 1100. By drawing on multiple resources in this way, the risk assessment module 1000 is able to make rapid and accurate risk assessment, and other, analyses. Of course, the combination of system inputs 700 employed in connection with embodiments of the invention may be varied as necessary to suit the requirements of a particular application and, accordingly, the system inputs disclosed herein are exemplary only and are not intended to limit the scope of the invention in any way.

Thus, a related aspect of embodiments of the invention is that they are highly flexible and adaptable in terms of the types, nature, and number of data sources and system inputs that may be employed in connection with implementation of the various methods and processes disclosed herein. More particularly, embodiments of the invention are well adapted for use in connection with currently known data sources, clinical and other criteria, system inputs, as well as for use in connection with diagnostic and predictive information, data sources, clinical and other criteria, and system inputs such as may be identified, developed, or further developed, in the future.

By way of example, viral and bacterial testing performed in connection with embodiments of the invention may include, among other things, testing for HHV 7, human metapneumoviruses, rhinoviruses as well as viruses that are as yet unknown. The diagnostics may include, in addition to PCR and DFA procedures, optical assays, clinical immunology tools such as enzyme-linked immunosorbent assays ("ELISA"), enhanced culture techniques and technologies not yet known or currently in a developmental stage. Further, testing of PCR for the detection of bacterial pathogens, to the extent such testing can be optimized, would allow rapid detection of bacterial pathogens (as quickly as 4-6 hours in some cases) and could readily be incorporated into the model, systems, processes and methods disclosed herein. As another example, analyses of cerebrospinal fluid profiles are expected to produce data that can be incorporated in various embodiments of the invention as a predictor of viral or bacterial infection.

In one exemplary implementation, the system inputs 700 include an EV PCR analysis of blood and cerebrospinal fluid ("CSF"), as well as a respiratory viral DFA test, which may be implemented as a nasal wash. These test results, in combination with the age of the subject and the bacteria culture results at multiple time points, such as 12, 24, 36 and 48 hours, are then used by the risk assessment module 1000 to assess, at these or other time points, the risk of serious bacterial infection in the subject. As suggested above, various other combinations of system input 700 may be employed consistent with the requirements of a particular application or protocol. Further details concerning various exemplary processes that may be implemented by the risk assessment module 1000 are provided below in connection with the discussion of FIGS. 9 and 10.

Assessments implemented in connection with the risk assessment module, or software and/or hardware of comparable functionality, can be performed quickly and reliably. Thus, many infants that were previously hospitalized due, for example, to uncertainty as to the presence of bacterial infection, can be released within 24 hours, thereby eliminating much of the expense associated with hospitalization, as well as avoiding the trauma that typically results for the infant and the parents when the infant is hospitalized. While these benefits are of particular interest to those hospitals devoted primarily to child and infant care, such benefits are of value to any facility involved in the treatment of infants and small children with fever.

In addition to generating various outputs 1100, such as a risk assessment 1102, reports 1104 and other outputs 1106, the risk assessment module 1000 may include various other functionalities as well. By way of example, some implementations of the risk assessment module 1000 include an alert functionality that notifies one or more designated client devices that test results have been received for a particular patient. The alert also includes, in some embodiments, particular information concerning the actual test results. One aspect of the alert functionality is that it permits the user of the client device, or client devices, to then initiate another risk assessment based upon the newly received patient information.

In addition, some embodiments of the risk assessment module 1000 may include links to other data and/or analytical modules. By way of example, information on adverse drug events in children could be linked to the risk assessment software. Further, the display of the risk factor, and related variables such as culture and viral diagnostic data can be customized to suit the desires of a particular user. Additionally, the risk factor and/or culture data, as a function of time or other variables, as well as viral diagnostic and other data, can be used to generate reports, graphs, analyses, and the like, which can then be printed and distributed as appropriate.

III. Aspects of Exemplary System Inputs

Figure 5:
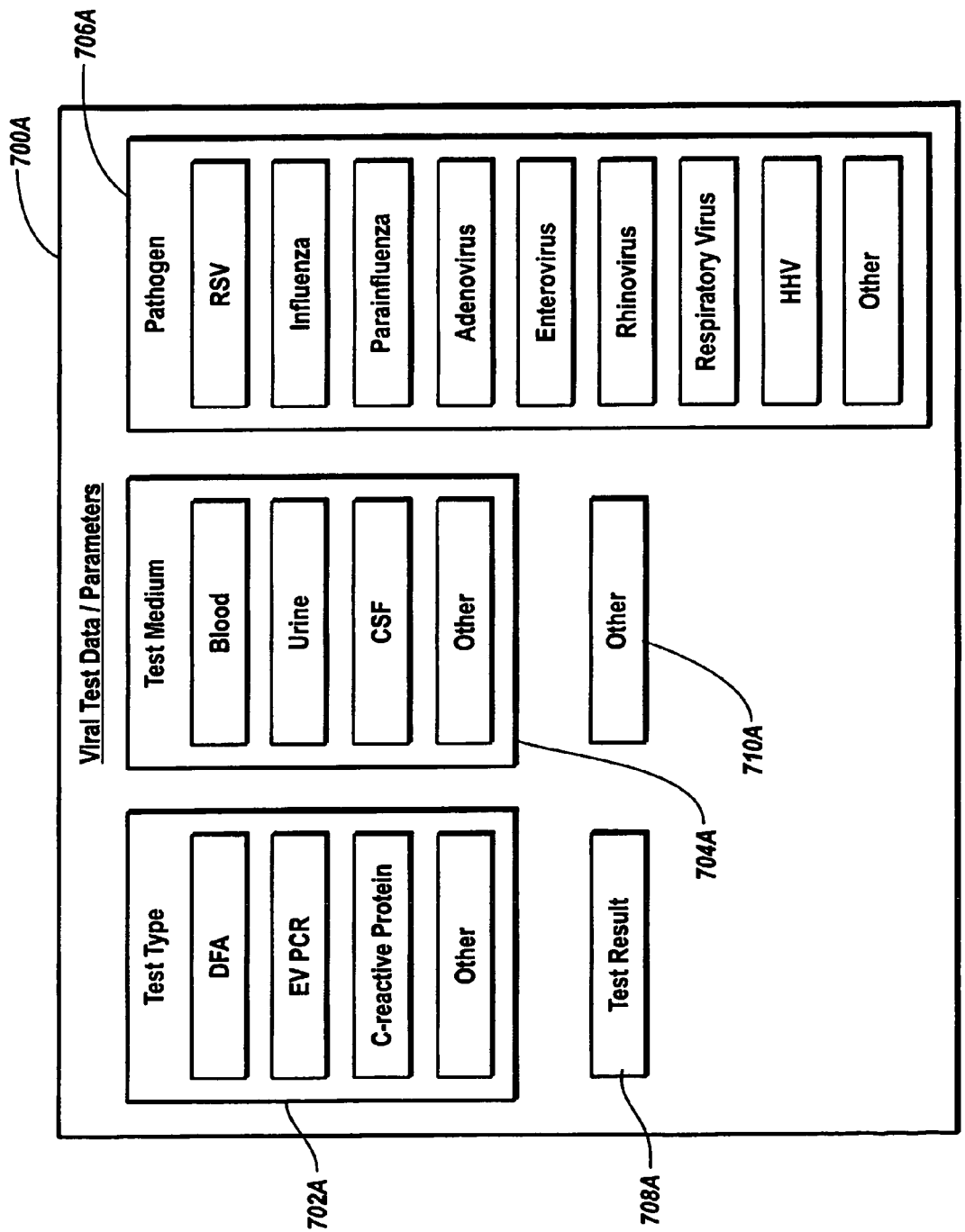
FIG. 5 is a block diagram that illustrates an exemplary grouping of viral test data and parameters that serve as inputs to the system illustrated in FIG. 4.

With attention now to FIG. 5, details are provided concerning various aspects of an exemplary set of viral test and parameters 700A such as may be employed by the risk assessment module 1000 in connection with the performance of risk assessment analyses and various other related functions. Generally, the exemplary grouping of viral test data and parameters 700A includes or relies upon various types of tests intended to confirm the presence, or lack, of a viral infection in the subject. Exemplarily, tests 702A include, but are not limited to, DFA, EV PCR, C-reactive protein and various other suitable tests. Both positive and negative viral diagnostic test results find application in embodiments of the invention.

Such viral diagnostic tests 702A are useful in a variety of circumstances. By way of example, one such aspect of the invention is a predictive, or risk assessment, feature which has been developed that indicates that if a particular subject tests positive for respiratory syncytial virus ("RSV") for example, that subject has about a one percent (1%) chance of having a bacterial infection. As another example, if a subject is enterovirus (EV) positive, such predictive tool indicates that the subject has about a five percent (5%) chance of having a concomitant bacterial infection.

Thus, the use of viral diagnostics tests to confirm the presence of a viral illness permit, in some cases at least, a user to predict or assess, what the risk is of that same subject having a concomitant bacterial illness. As noted earlier, this is a useful feature at least because it is known that bacterial illness is presently the most serious cause of febrile episodes. Thus, the ability to predict bacterial illness corresponds closely with an ability to quickly and reliably predict outcomes of febrile episodes.

Additionally, because viral illnesses occur during various seasons, the presence of a particular type of virus can likewise be used as an aid to predict the likelihood of a concomitant bacterial illness. As discussed in further detail herein, this feature of the invention, used in conjunction with 'time to positivity' for various bacterial cultures, permits reliable assessments to be quickly made as to the risk that a bacterial illness, and fever, will occur in a given subject in a given period of time. With continuing reference now to FIG. 5, tests 702A may be performed in connection with various test media 704A obtained from the patient such as, but not limited to, blood, urine, CSF and/or various other materials. Generally, the various test types 702A can be selected to confirm the presence, or lack, of a variety of viral pathogens, such as those indicated at 706A. Exemplary viral pathogens 706A that may be tested for in connection with the implementation of embodiments of the invention include, but are not limited to, RSV, influenza, parainfluenza, adenovirus, enterovirus, rhinovirus, respiratory virus, HHV, as well as various other virus. Such tests are particularly useful in that, presently, RSV, Influenza A and B, parainfluenza 1, 2, and 3 and adenovirus, collectively, may cause up to 60% of febrile episodes in children.

Another aspect of the exemplary viral test data and parameters 700A are the test results 708A that are obtained from conducting the test 702A. As discussed elsewhere herein, viral diagnostic test results 708A are particularly useful in some implementations of the invention. Finally, the viral test data and parameters 700A may include various other test data and parameters 710A as well such as, but not limited to, viral epidemiology. Accordingly, the scope of the invention should not be construed to be limited to the exemplary viral test data and parameters 700A indicated in FIG. 5. More generally, the particular combination of viral test data and parameters 700A to be employed may be defined and selected as necessitated by the requirements of a particular application or situation.

Figure 6:
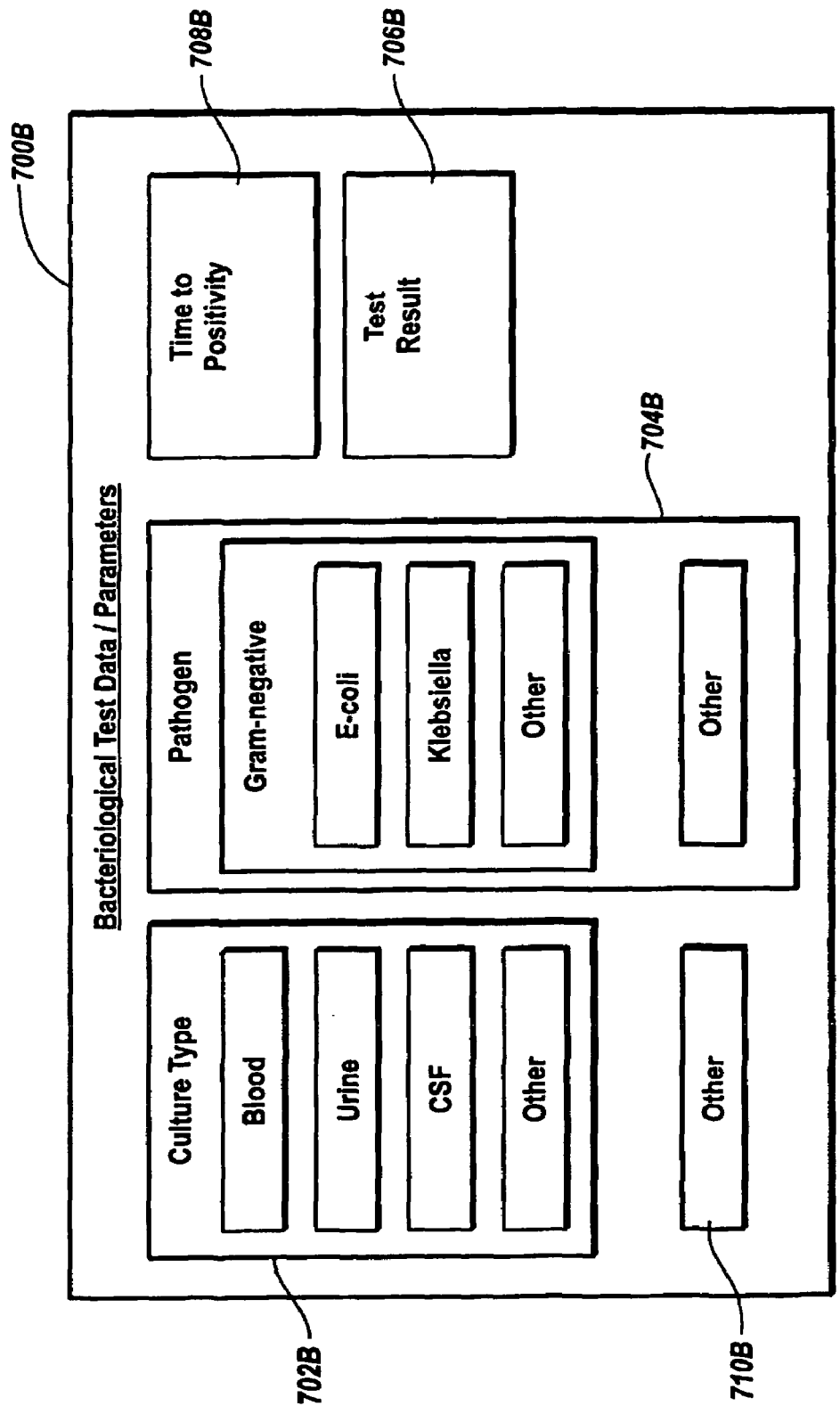
FIG. 6 is a block diagram that illustrates an exemplary grouping of bacteriological test data and parameters that serve as inputs to the system illustrated in FIG. 4.

As noted earlier, at least some implementations of the risk assessment module 1000 use various bacteriological test data and parameters as aids in facilitating the risk assessment analysis and other processes. With attention now to FIG. 6, details are provided concerning some exemplary bacteriological test data and parameters 700B that may be employed in this regard. As indicated in FIG. 6, various culture types 702B may be employed. Examples of bacterial culture types 702B include, but are not limited to, blood, urine, and CSF.

Aspects of bacterial cultures that have proven useful include their incubation time and 'time to positivity.' Exemplarily, blood is incubated for about 5 days, urine is incubated for about 2 days, and spinal fluid is incubated for about 3 days. Analyses of this data shows that for the average blood culture, a bacterial pathogen will manifest itself, if at all, in about 16 hours, this is the 'time to positivity' for that blood culture. The time to positivity for urine and CSF cultures is about 12 hours.

Additionally, the bacteriological test data and parameters 700B generally concern one or more pathogens 704B that are of interest in the risk assessment analysis. Exemplary pathogens include Gram-negative such as *E. coli* or *Klebsiella oxytoca*, as well as various other Gram-negative bacteriological pathogens, and non Gram-negative pathogens.

It should be noted in this regard that, in contrast with the Rochester criteria, for example, which are concerned in large part with the treatment of diseases that have been substantially eliminated with immunization and antibiotic prophylaxis (such as Group B Streptococcal infection and *Haemophilus influenza* type B), some exemplary embodiments of the present invention are directed to the treatment of bacterial caused fever that, unlike Group B Streptococcal infection and *Haemophilus influenza* type B, have not, as yet, been substantially eliminated. Examples of such Gram-negative bacteria are *E. coli* and *Klebsiella oxytoca*. Because such bacterial infections have not been substantially eliminated by immunization and antibiotic prophylaxis, they simply must be treated when they occur. In addition to testing for Gram-negative bacterial pathogens, various other bacteria may likewise be investigated.

Other factors that are of particular interests with respect to the bacteriological test data parameters 700B include any bacteriological test results 706B as well as the 'time to positivity' 708B if a particular test turns out to be positive. In connection with the foregoing, it should be noted that both positive and negative bacteriological test results find application in embodiments of the invention. Of course, such bacteriological test data and parameter 700B are exemplary only and various other bacteriological test data, parameters and information 710B, such as bacterial epidemiology, may additionally or alternatively be employed, as may be necessitated by the requirements of a particular application or set of circumstances.

In addition to the use of various viral and bacteriological test data, parameters and other information, various clinical criteria, such as the Rochester criteria, may also be employed in connection with analyses and other processes performed by the risk assessment module 1000. For example, one logistical regression analysis performed on a group of 1400 infants with standard Rochester scoring has identified three factors that are predictive of Gram-negative bacterial infection. One or more of such factors may be incorporated within at least some embodiments of the invention, and include, history of chronic illness (odds ratio ("OR") 6.3 95% CI 2.6-15), bandemia (OR 3 95% CI 1.7-5.2), and abnormal urinalysis (OR 18 95% CI 8.5-37), each with $p<0.0001$). Other analyses of the Rochester criteria may provide similarly useful results.

Figure 7:
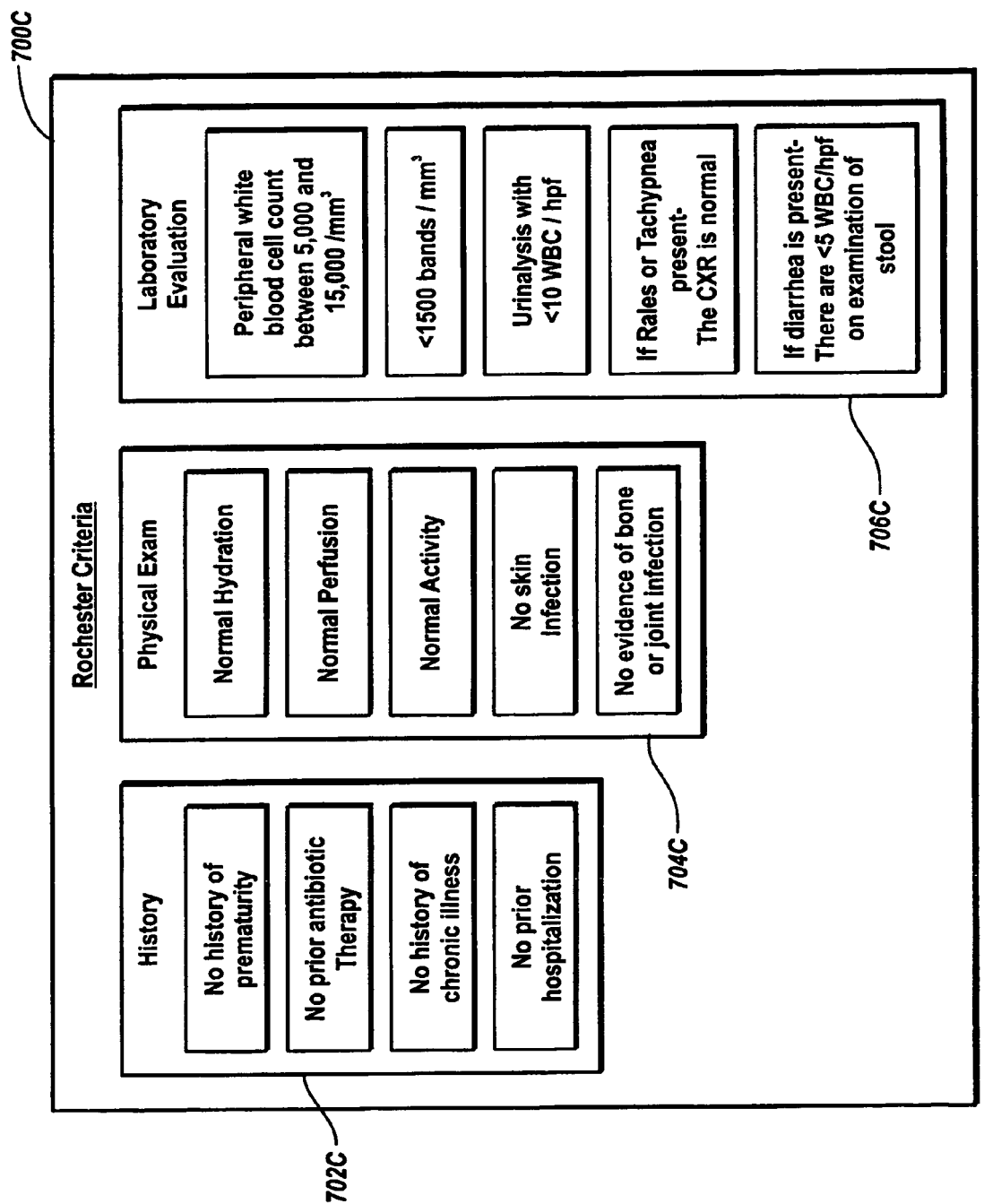
FIG. 7 is a block diagram that illustrates the various Rochester criteria.

With attention now to FIG. 7, the Rochester criteria 700C can generally be grouped into three different areas. These areas concern the history 702C of the patient, a physical exam 704C of the patient, as well as a laboratory evaluation 706C of the patient. Depending upon the particular implementation, less than all of the Rochester criteria may be employed in some cases.

The history 702C of the patient generally refers to the prior medical history of the patient and includes the criteria: (i) no history of prematurity; (ii) no prior antibiotic therapy; (iii) no history of chronic illness; and, (iv) no prior hospitalization. The physical exam 704C portion of the Rochester criteria 700C includes the following criteria: (i) normal hydration; (ii) normal perfusion; (iii) normal activity; (iv) no skin infection; and, (v) no evidence of bone or joint infection. Finally, the laboratory evaluation criteria 706C include: (i) peripheral white blood cell count between 5000 and 15,000 per cubic millimeter (mm3); (ii) less than 1500 bands per mm3; (iii) urinalysis with less than 10 WBC/hpf; (iv) if rales or tachypnea is present—the CXR is normal; and, (iv) if diarrhea is present—there are less than 5 WBC/hpf on examination of the stool.

Various other factors may likewise be considered for use in connection with the analyzes and other processes performed by the risk assessment module 1000. Among other things, these other factors can be advantageously employed to permit a high degree of customization of the data contained in a particular data base accessed by the risk assessment module 1000, and also permit the performance of the risk assessment 1000 to be finely tuned to highly particularized situations or sets of circumstances. Thus, these and other factors lend a high degree of flexibility to embodiments of the invention in terms of the analyses and other processes that may be performed, and in terms of the results obtained.

Figure 8:
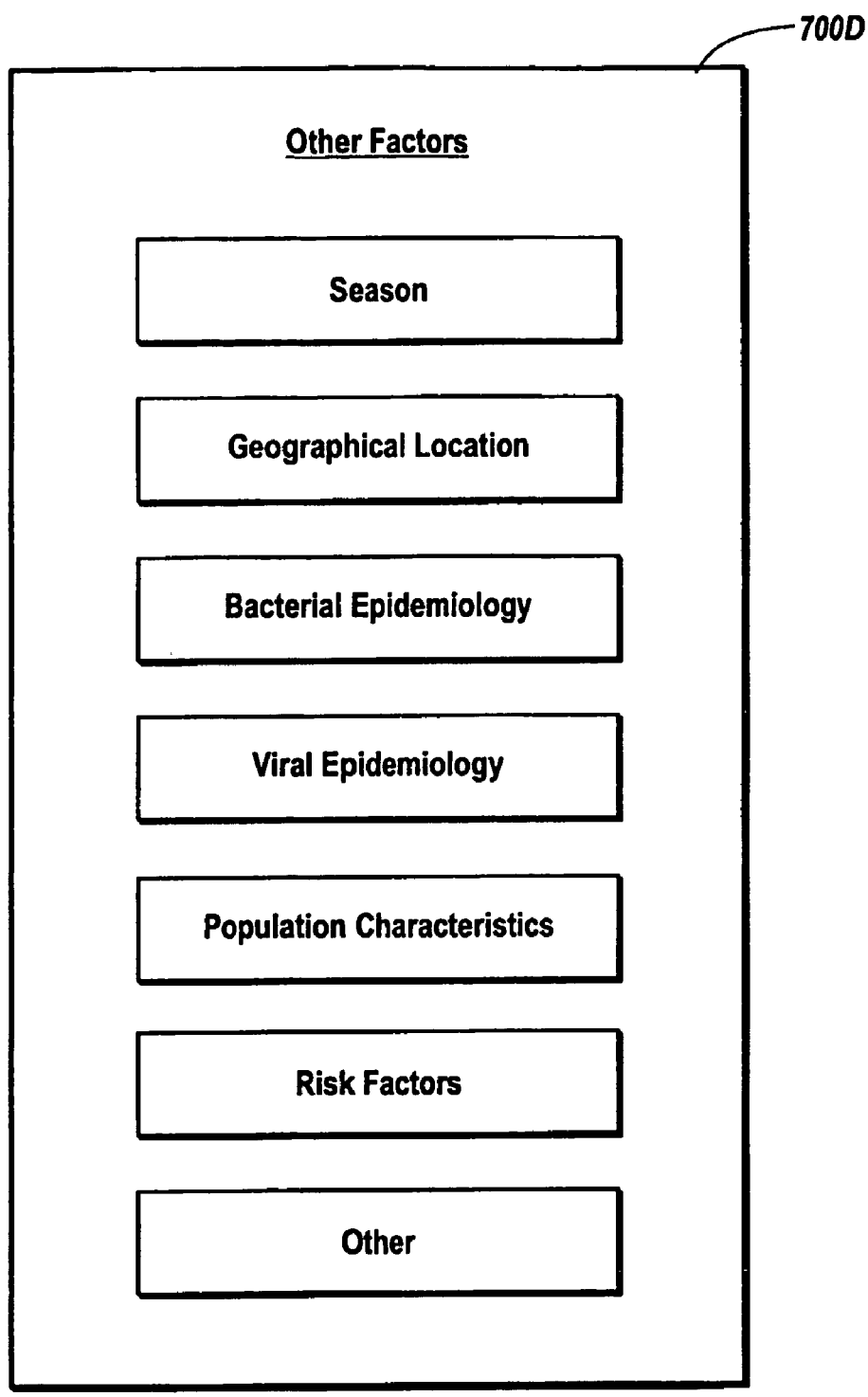
FIG. 8 is a block diagram that illustrates an exemplary grouping of various other factors that may serve as inputs to the system illustrated in FIG. 4.

With particular attention now to FIG. 8, various examples of such factors 700D are considered. As indicated there, such factors 700D may include, but are not limited to, a particular season of the year, a geographical location, information concerning bacterial epidemiology and viral epidemiology, various selected population characteristics, known or expected risk factors, and any other factor that may be useful to consider in connection with the processes and analyses performed by way of the risk assessment module 1000.

IV. Aspects of Exemplary Treatment Protocols and Related Rules and Procedures

Figure 9:
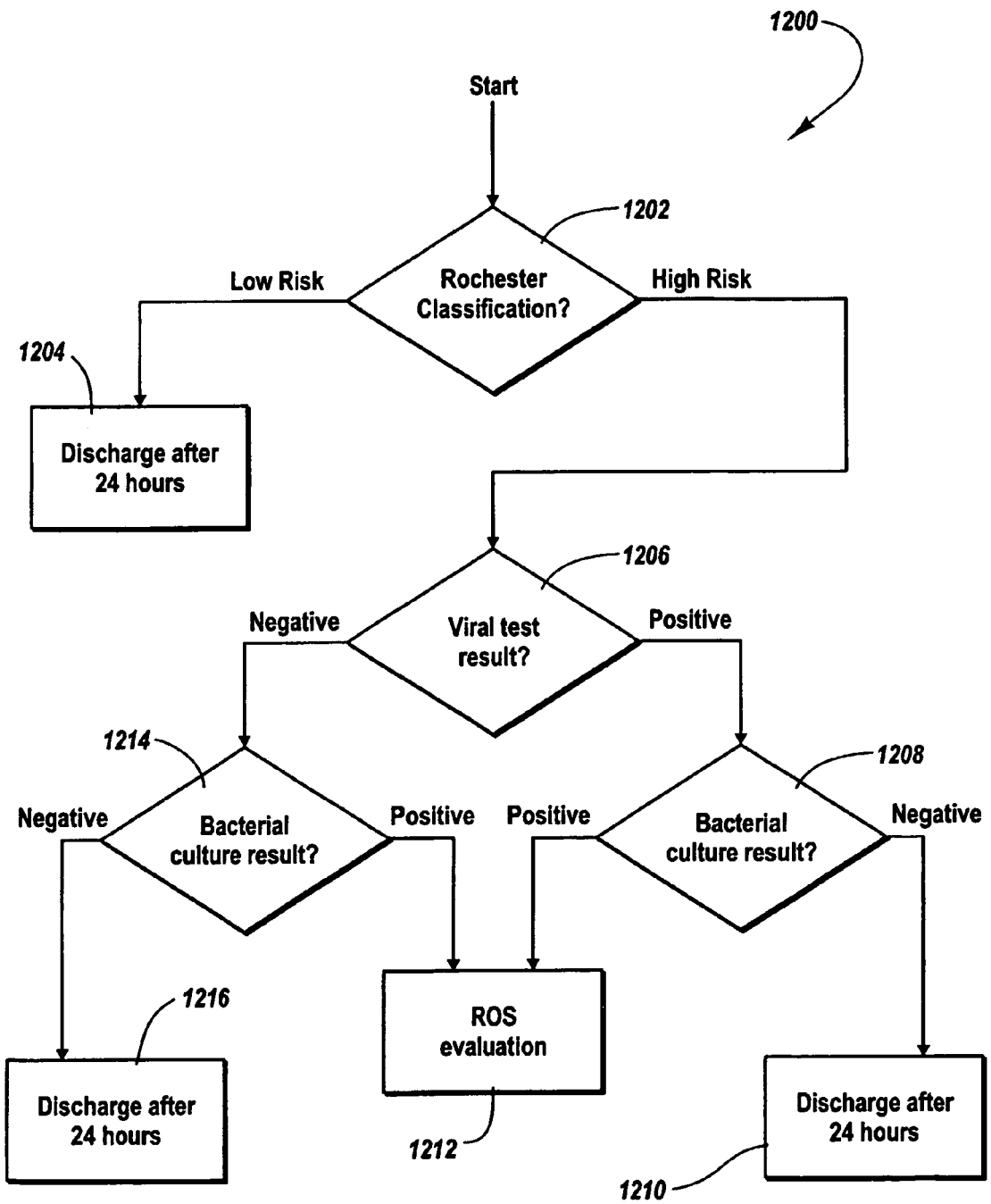
FIG. 9 is a flow diagram illustrating various aspects of an exemplary treatment protocol such as may be employed in connection with the treatment of young febrile infants.

Directing attention now to FIG. 9, details are provided concerning one exemplary treatment protocol such as may be designed and implemented in connection with the structure and functionality disclosed herein. As discussed above, some exemplary treatment protocols comprise a process that guides a practitioner in medical diagnosis and treatment. The treatment protocol may be developed in various ways. In some cases, the treatment protocol is developed empirically based upon data analysis.

Further, some treatment protocols may simply specify actions to be taken, where the rationale underlying the specified action is based on analysis of data and other information. In other cases, treatment protocols may present the treating physician with specific data or information that can be used to inform and guide the making of a particular decision. One example of such specific data, discussed above, the chance, expressed as a percentage, that a particular condition will occur, in view of various system inputs or other information. In cases such as these, the treating physician can then bring his or her experience and judgment to bear on what action(s) should be taken in light of the numbers presented.

Yet other treatment protocols employ a combination of the aforementioned, and/or other, approaches. One such approach is exemplified by a protocol that provides raw numbers to the treating physician, but also provides general decisional guidelines to the treating physician that are indexed to particular values, or ranges of values, of the raw numbers that have been presented. In any case, processes such as those examples illustrated in FIGS. 9 and 10 may be used to develop, or further develop, a body of data from which conclusions can be made as to, for example, the probabilities of occurrence of viral and bacteriological conditions, which probabilities can then be used to calculate a risk of occurrence of particular conditions.

In general, the exemplary process 1200 illustrated in FIG. 9 in concerned with the identification of the risk of serious bacterial infection in febrile infants that are ninety (90) days old or younger. As further indicated in FIG. 9, this implementation of process 1200 makes use of the Rochester criteria, as well as viral and bacterial test results. As noted elsewhere herein however, various other protocols and procedures may use additional and/or alternative system inputs as well.

The process 1200 begins at stage 1202 wherein assessment is made as to whether or not the infant is classified at 'high risk' or 'low risk' for bacterial infection, as determined by one or more of the Rochester criteria. If it is determined at decision point 1202 that the infant is at low risk, the process 1200 advances to stage 1204 and the infant is discharged after a predetermined time period, such as 24 hours. On the other hand, if a determination is made at the decision point 1202 that the infant is at high risk for bacterial infection, the process advances to stage 1206.

At stage 1206, a decision point is reached where a determination is made that relates to the outcome of a viral diagnostic test. If the viral diagnostic test results are positive, the process 1200 advances to stage 1208 where a determination is made that relates to the results of a bacterial cultural test. If the bacterial cultural test is determined at stage 1208 to be negative, the process advances to stage 1210 and then the infant is discharged after a predetermined time period, such as 24 hours. If, on the other hand the bacterial culture result is determined at stage 1208 to be positive, the process advances to stage 1212 where an ROS evaluation is performed.

If, on the other hand it is determined at stage 1206 that the viral diagnostic test result is negative, the process advances to stage 1214 where a determination is made concerning the results of a bacterial diagnostic test. If the bacterial culture result is positive, the process advances to stage 1212 where an ROS evaluation is performed. Alternatively, if it is determined at stage 1214 that the bacterial culture result is negative, the process advances to stage 1216 and the infant is discharged after a predetermined time period, such as 36 hours.

It should be noted in connection with the exemplary process 1200 illustrated in FIG. 9, that some or all aspects of the process may be repeated at predetermined time intervals. By way of example, stages 1208 and 1214 where determinations are made as to the result of the bacterial culture may be repeated every 12 hours and/or until positivity is determined. Accordingly, the time periods indicated in FIG. 9 are exemplary only and should not be construed to limit the scope of the invention in any way. More generally, some or all aspects of processes such as process 1200 may be repeated on any basis that may prove useful in the diagnosis and treatment of the subject.

Figure 10:
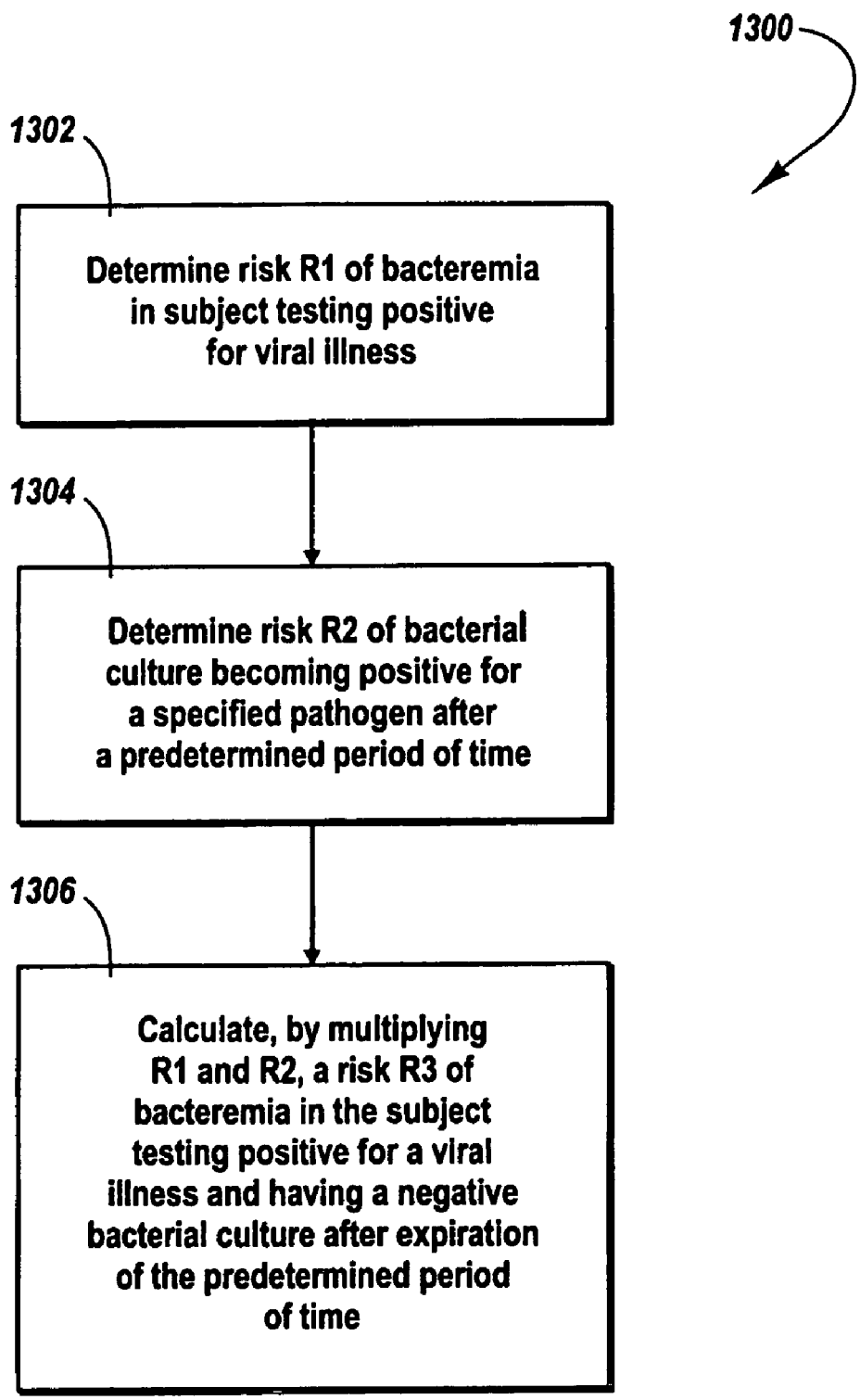
FIG. 10 is a flow diagram illustrating an exemplary process for calculating the risk of occurrence of a particular condition, such as a serious pathologic infection, in a patient.

With attention now to FIG. 10, details are provided concerning another exemplary treatment protocol 1300 suitable for use in connection with performance of medical diagnoses and treatments. As indicated there, stage 1302 of the process is concerned with determining a risk, denoted at R1, of the occurrence of bacteremia in a subject that has tested positive for viral illness. Exemplarily, the risk R1 is statistically determined, with particular reference to viral illness data contained in the database. The process then advances to stage 1304 where a risk, denoted at R2, of a bacterial culture becoming positive, for a specified pathogen, after a predetermined time period. Similar to the determination of R1, the risk R2 is statistically determined, with particular reference to bacterial culture data contained in the database.

Once risks R1 and R2 have been determined, the process 1300 advances to stage 1306 where a risk R3 is determined, calculated in this case, by multiplying risks R1 and R2. In particular, risk R3 represents the risk of bacteremia occurring in any given subject testing positive for a viral illness and having a negative bacterial culture after expiration of a predetermined period of time. In view of the known value of risk R3, the treating physician can then make a treatment decision concerning the subject. Thus, one aspect of embodiments of treatment protocols such as those depicted in FIGS. 9 and 10 is that while the risk assessment module, methods, systems and associated software provide the treating physician with various useful information, data, and decision guidelines, the decision as to the course of action to be taken with respect to a particular patient nonetheless remains within the clinical judgment of the physician. Thus, while one physician may decide that a particular risk level is acceptable, another physician may prefer a different risk threshold. Accordingly, the risk assessment method, and associated software, of the present invention can be effectively employed in conjunction with a wide variety of medical practice styles.

V. Aspects of Exemplary Hardware and Software, and Associated Configurations

As suggested earlier, embodiments of the present invention may be implemented in connection with computing environments that include a variety of systems, devices, hardware and software. More detailed information is now provided concerning exemplary hardware and software, and related configurations, that may be used to implement one or more aspects of embodiments of the invention. Embodiments within the scope of the present invention also include computer-readable media for carrying or having computer-executable instructions or electronic content structures stored thereon. Such computer-readable media can be any available media which can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or electronic content structures and which can be accessed by a general purpose or special purpose computer.

When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media. Computer-executable instructions comprise, for example, instructions and content that cause a general purpose computer, special purpose computer, or special purpose processing device to perform a certain function or group of functions.

The following discussion is intended to provide a brief, general description of an exemplary computing environment in which the invention may be implemented. Although not required, aspects of the invention may be described in the general context of computer-executable instructions, such as program modules, being executed by computers in network or other environments. Generally, program modules include routines, programs, objects, components, and content structures that perform particular tasks or implement particular abstract content types. Computer-executable instructions, associated content structures, and program modules represent examples of the program code means for executing steps of the methods disclosed herein. The particular sequence of such executable instructions or associated content structures represent examples of corresponding acts for implementing the functions described in such steps.

Of course, the invention may be practiced in network computing environments with many types of computer system configurations, including personal computers, hand-held devices such as tablets and personal data assistants ("PDA"), multi-processor systems, microprocessor-based or programmable consumer electronics, network PCs, minicomputers, mainframe computers, and the like. Exemplary network computing environments include, but are not limited to, local area networks ("LAN"), wide area networks ("WAN"), as well as computing environments implemented or defined in connection with global computer networks such as the Internet.

One exemplary computing environment comprises a client-server arrangement implemented within the context of a global computer network. Exemplarily, the client-server arrangement includes a web server located at a medical facility and configured so that the web server can be accessed, and/or otherwise interact with, various portable and/or remote computing devices such as those disclosed herein, wherein the portable or remote devices may be employed at the medical facility where the web server is located, and/or may be employed at other locations.

Additionally, or alternatively, the computing environment may include one or more web servers residing in locations remote from an identified medical facility. Among other things, a web-based implementation of aspects of the invention enhances flexibility, accessibility and permits users to have ready access to complete, and up-to-date information. The web server also provides a central location for receiving/transmitting data and information from/to the users of the system, as well as providing for ready and reliable synchronization of data and other information and materials between and among the various users and the web server.

The invention may also be practiced in distributed computing environments where tasks are performed by local and remote processing devices that are linked (either by hardwired links, wireless links, or by a combination of hardwired or wireless links) through a client network. In a distributed computing environment for example, program modules may be located in both local and remote memory storage devices.

The described embodiments are to be considered in all respects only as exemplary and not restrictive. The scope of the invention is, therefore, indicated by the appended claims rather than by the foregoing description. All changes which come within the meaning and range of equivalency of the claims are to be embraced within their scope.

What is claimed is:

1. A method for performing a risk assessment concerning a subject, the method being implemented in connection with a computing environment having a database associated therewith, and the method comprising:
   receiving results of a viral diagnostic test;
   receiving a status of a culture for identifying the existence or absence of at least one bacterial pathogen;
   receiving results of a clinical analysis;
   determining a risk of occurrence, in the subject, of a particular condition of interest, the risk determination being based at least in part upon: results of the viral diagnostic test; the clinical analysis; and, the status of the culture for identifying the existence or absence of at least one bacterial pathogen; and
   correlating the risk of occurence of the particular condition with at least one action.

2. The method as recited in claim 1, wherein receiving results of a viral diagnostic test comprises receiving results from one of the following tests: EV PCR, and DFA.

3. The method as recited in claim 1, wherein the status of the culture is received on a periodic basis.

4. The method as recited in claim 1, wherein the risk determination is made on a periodic basis.

5. The method as recited in claim 1, wherein receiving results of a clinical analysis comprises receiving results of at least one Rochester criterion.

6. The method as recited in claim 1, further comprising receiving a status of at least one of: hydration, and band count of the subject.

7. The method as recited in claim 1, wherein determining a risk of occurrence, in the subject, of a particular condition of interest comprises determining the risk of serious bacterial infection in the subject.

8. The method as recited in claim 1, further comprising generating an alert when culture status or test results are received.

9. The method as recited in claim 1, further comprising uploading test results and culture status to the database.

10. The method as recited in claim 1, further comprising uploading the determined risk of occurrence to the database.

11. A computer program product for implementing a method for performing a risk assessment concerning a subject, the computer program product being suitable for use in connection with a computing environment having a database associated therewith, and the computer program product comprising:
    a computer readable medium carrying computer executable instructions for performing the method, wherein the method comprises:
    receiving results of a viral diagnostic test;
    receiving a status of a culture for identifying the existence or absence of at least one bacterial pathogen;
    receiving results of clinical analysis; and
    determining a risk of occurrence, in the subject, of a particular condition of interest, the risk determination being based at least in part upon: results of the viral diagnostic test; the clinical analysis; and, the status of the culture for identifying the existence or absence of at least one bacterial pathogen; and
    correlating the risk of occurence of the particular condition with at least one action.

12. The computer program product as recited in claim 11, wherein receiving results of a viral diagnostic test comprises receiving results from one of the following tests: EV PCR, and DFA.

13. The computer program product as recited in claim 11, wherein the status of the culture is received on a periodic basis.

14. The computer program product as recited in claim 11, wherein the risk determination is made on a periodic basis.

15. The computer program product as recited in claim 11, wherein receiving results of a clinical analysis comprises receiving results of at least one Rochester criterion.

16. The computer program product as recited in claim 11, further comprising receiving a status of at least one of: hydration, and band count of the subject.

17. The computer program product as recited in claim 11, wherein determining a risk of occurrence, in the subject, of a particular condition of interest comprises determining the risk of serious bacterial infection in the subject.

18. The computer program product as recited in claim 11, further comprising generating an alert when culture status or test results are received.

19. The computer program product as recited in claim 11, further comprising uploading test results and culture status to the database.

20. The computer program product as recited in claim 11, further comprising uploading the determined risk of occurrence to the database.

21. A method for performing a risk assessment concerning a subject, the method being implemented in connection with a client-server computing environment, and the method comprising:
    receiving results of a viral diagnostic test selected from the group consisting of: EV PCR, and DFA;
    receiving results of a clinical analysis;

receiving a status of at least one of: hydration, band count, and a culture for identifying the existence or absence of at least one bacterial pathogen; and determining a risk of occurrence, in the subject, of a particular condition of interest, the risk determination being based at least in part upon: results of the viral diagnostic test; the clinical analysis; and, the status of one or more of the hydration, band count, and culture for identifying the existence or absence of at least one bacterial pathogen.

22. The method as recited in claim 21, wherein receiving results of a viral diagnostic test comprises receiving results of a viral diagnostic test for at least one of: enterovirus, RSV, Influenza A, Influenza B, parainfluenza 1, parainfluenza 2, parainfluenza 3, adenovirus, HHV 6, and rhinovirus.

23. The method as recited in claim 21, wherein receiving a status concerning a culture for identifying the existence or absence of at least one bacterial pathogen comprises receiving status of a culture for identifying a Gram-negative bacterial pathogen.

24. The method as recited in claim 21, wherein receiving a status concerning a culture for identifying the existence or absence of at least one bacterial pathogen comprises receiving status of at least one of: a blood culture for identifying at least one bacterial pathogen; a urine culture for identifying at least one bacterial pathogen; and a cerebrospinal fluid culture for identifying at least one bacterial pathogen.

25. The method as recited in claim 21, further comprising correlating the risk of occurrence of the particular condition with at least one action.

26. The method as recited in claim 21, wherein receiving results of a clinical analysis comprises receiving results of at least one Rochester criterion.

27. A computer program product for implementing a method for performing a risk assessment concerning a subject, the computer program product comprising:

a computer readable medium carrying computer executable instructions for performing the method, wherein the method comprises:

receiving results of a viral diagnostic test selected from the group consisting of: EV PCR, and DFA;

receiving results of a clinical analysis;

receiving a status of at least one of: hydration, band count, and a culture for identifying the existence or absence of at least one bacterial pathogen; and determining a risk of occurrence, in the subject, of a particular condition of interest, the risk determination being based at least in part upon: results of the viral diagnostic test; the clinical analysis; and, the status of one or more of the hydration, band count, and culture for identifying the existence or absence of at least one bacterial pathogen.

28. The computer program product as recited in claim 27, wherein receiving results of a viral diagnostic test comprises receiving results of a viral diagnostic test for at least one of: enterovirus, RSV, Influenza A, Influenza B, parainfluenza 1, parainfluenza 2, parainfluenza 3, adenovirus, HHV 6, and rhinovirus.

29. The computer program product as recited in claim 27, wherein receiving a status concerning a culture for identifying the existence or absence of at least one bacterial pathogen comprises receiving status of a culture for identifying a Gram-negative bacterial pathogen.

30. The computer program product as recited in claim 27, wherein receiving a status concerning a culture for identifying the existence or absence of at least one bacterial pathogen comprises receiving status of at least one of: a blood culture for identifying at least one bacterial pathogen; a urine culture for identifying at least one bacterial pathogen; and a cerebrospinal fluid culture for identifying at least one bacterial pathogen.

31. The computer program product as recited in claim 27, further comprising correlating the risk of occurrence of the particular condition with at least one action.

32. The computer program product as recited in claim 27, wherein receiving results of a clinical analysis comprises receiving results of at least one Rochester criterion.

33. A method for performing a risk assessment concerning a subject, the method being implemented in connection with a client-server computing environment, and the method comprising:

receiving results of a DFA viral diagnostic test that tests for at least one of: enterovirus, RSV, Influenza A, Influenza B, parainfluenza 1, parainfluenza 2, parainfluenza 3, adenovirus, HHV 6, and rhinovirus;

receiving results of a Rochester criteria analysis;

receiving a status of at least one of: hydration, band count, a blood culture for identifying the existence or absence of at least one bacterial pathogen, a urine culture for identifying the existence or absence of at least one bacterial pathogen, and a cerebrospinal fluid culture for identifying the existence or absence of at least one bacterial pathogen; and calculating a risk of occurrence, in the subject, of a bacterial infection, using: results of the DFA viral diagnostic test; the Rochester criteria analysis; and, the status of at least one of said blood, urine, and cerebrospinal fluid cultures, hydration, and band count.

34. The method as recited in claim 33, further comprising transmitting the risk of occurrence to a client device.

35. The method as recited in claim 33, further comprising correlating the risk of occurrence of the particular condition with at least one action.

36. A computer program product for implementing a method for performing a risk assessment concerning a subject, the computer program product being suitable for use in connection with a client-server computing environment, and the computer program product comprising:

a computer readable medium carrying computer executable instructions for performing the method, wherein the method comprises:

receiving results of a DFA viral diagnostic test that tests for at least one of: RSV, Influenza A, Influenza B, parainfluenza 1, parainfluenza 2, parainfluenza 3, adenovirus, HHV 6, and rhinovirus;

receiving results of a Rochester criteria analysis;

receiving a status of at least one of: hydration, band count, a blood culture for identifying the existence or absence of at least one bacterial pathogen, a urine culture for identifying the existence or absence of at least one bacterial pathogen, and a cerebrospinal fluid culture for identifying the existence or absence of at least one bacterial pathogen; and calculating a risk of occurrence, in the subject, of a bacterial infection, using: results of the DFA viral diagnostic test; the Rochester criteria analysis; and, the status of at least one of said blood, urine, and cerebrospinal fluid cultures, hydration, and band count.

37. The computer program product as recited in claim 36, further comprising transmitting the risk of occurrence to a client device.

38. The computer program product as recited in claim 36, further comprising correlating the risk of occurrence of the particular condition with at least one action.

39. A method for calculating a risk that a particular condition will occur in a subject, the method being implemented in connection with a client-server environment having a database associated therewith, the database including viral illness data and bacterial culture data for a plurality of subjects, and the method comprising:
   determining, from the viral illness data of the database, a risk R1 of bacteremia in any given subject testing positive for a viral illness;
   determining, from the bacterial culture data of the database, a risk R2 of a bacterial culture becoming positive for a specified pathogen after a predetermined time period; and
   calculating, by multiplying risks R1 and R2 together, a risk R3 of bacteremia in any given subject testing positive for a viral illness and having a negative bacterial culture after expiration of the predetermined time period.

40. The method as recited in claim 39, further comprising transmitting the risk of bacteremia to a client device.

41. The method as recited in claim 39, further comprising correlating the risk of bacteremia with at least one action.

42. A computer program product for implementing a method for performing a risk assessment concerning a subject, the computer program product being configured to receive data from a database that includes viral illness data and bacterial culture data for a plurality of subjects, the computer program product comprising:
   a computer readable medium carrying computer executable instructions for performing the method, wherein the method comprises:
   determining, from the viral illness data of the database, a risk R1 of bacteremia in any given subject testing positive for a viral illness;
   determining, from the bacterial culture data of the database, a risk R2 of a bacterial culture becoming positive for a specified pathogen after a predetermined time period; and
   calculating, by multiplying risks R1 and R2 together, a risk R3 of bacteremia in any given subject testing positive for a viral illness and having a negative bacterial culture after expiration of the predetermined time period.

43. The computer program product as recited in claim 42, further comprising transmitting the risk of bacteremia to a client device.

44. The computer program product as recited in claim 42, further comprising correlating the risk of bacteremia with at least one action.

45. A method for facilitating development of a treatment protocol, the method being implemented in connection with a computing environment having a database associated therewith that includes viral illness data and bacterial culture data for a plurality of subjects, the method comprising:
   accessing viral infection test results from the viral illness data, the viral infection test results including at least one of an EV PCR and DFA test result for each of the plurality of subjects;
   accessing time to positivity data from the bacterial culture data, the time to positivity data including the results of at least one of a urine, blood, and CSF culture for each of the plurality of subjects;
   statistically analyzing the accessed viral infection test results and the accessed time to positivity data to identify the occurrence of viral infections and the occurrence bacterial infections in the plurality of subjects;
   assessing, based upon the statistical analysis, the risk of a subject that has a viral illness also having a concomitant bacterial illness; and
   using the risk assessment to define a rule suitable for use as part of the treatment protocol for treating subsequent subjects at risk for bacterial infection.

46. The method as recited in claim 45, wherein statistically analyzing the accessed viral infection test results and the accessed time to positivity data comprise using Bayesian analysis techniques.

47. A computer program product for use in a computer system, the computer program product for implementing a method for facilitating development of a treatment protocol, the computer program product being configured to receive data from a database that includes viral illness data and bacterial culture data for a plurality of subjects, and the computer program product comprising:
   a recordable-type computer readable medium carrying computer executable instructions that, when executed at a processor, cause the computer system to perform the method, including the following:
   accessing viral infection test results from the viral illness data, the viral infection test results including at least one of an EV PCR and DFA test result for each of the plurality of subjects;
   accessing time to positivity data from the bacterial culture data, the time to positivity data including the results of at least one of a urine, blood, and CSF culture for each of the plurality of subjects;
   statistically analyzing the accessed viral infection test results and the accessed time to positivity data to identify the occurrence of viral infections and the occurrence bacterial infections in the plurality of subjects;
   assessing, based upon the statistical analysis, the risk of a subject that has a viral illness also having a concomitant bacterial illness; and
   using the risk assessment to define a rule suitable for use as part of the treatment protocol for treating subsequent subjects at risk for bacterial infection.

48. The computer program product as recited in claim 47, wherein statistically analyzing the accessed viral infection test results and the accessed time to positivity data comprise using Bayesian analysis techniques.

49. In a computing environment having a database associated therewith, a method for refining an assessment of risk for bacterial infection in a febrile infant as medical information for the febrile infant becomes available, the method comprising:
   an act of accessing Rochester criteria data including historical data and physical examination data corresponding to a febrile infant;
   an act of assessing a risk of occurrence of a bacterial infection in the febrile infant based on the historical data and physical examination data;
   an act of accessing Rochester criteria data including laboratory result data corresponding to the febrile infant subsequent to accessing the Rochester criteria data including the historical data and the physical examination data;
   an act of re-assessing the risk of occurrence of a bacterial infection in the febrile infant based on the laboratory result data in combination with the historical data and the physical examination data;
   an act of accessing viral diagnostic test result data corresponding to the febrile infant subsequent to accessing the Rochester criteria data including the laboratory result data;
   an act of re-assessing the risk of occurrence of a bacterial infection in the febrile infant based on the viral diagnostic test result data in combination with the laboratory result data, the historical data, and the physical examination data;

an act of accessing bacterial culture result data corresponding to the febrile infant subsequent to accessing the viral diagnostic test result data; and an act of re-assessing the risk of occurrence of a bacterial infection in the febrile infant based on the bacterial culture result data in combination with the viral diagnostic result data, the laboratory result data, the historical data, and the physical examination data.

50. The method as recited in claim 49, wherein the act of accessing Rochester criteria data including historical data and physical examination data corresponding to a febrile infant comprises an act accessing one or more of history of prematurity and history of chronic illness corresponding to the febrile infant.

51. The method as recited in claim 50, wherein the act of assessing a risk of occurrence of a bacterial infection in the febrile infant based on the historical data and physical examination data comprises an act of assessing the risk of occurrence of a bacterial infection in the febrile infant based on one or more the history of prematurity and the history of chronic illness corresponding to the febrile infant.

52. The method as recited in claim 51, wherein the act of an act of accessing Rochester criteria data including laboratory result data corresponding to the febrile infant comprises an act accessing one or more of a white blood cell count, a band count, and urinalysis result data.

53. The method as recited in claim 52, wherein the act accessing one or more of a white blood cell count, a band count, and urinalysis result data comprises an act of accessing a white blood cell count that is one of less than 5,000/mm$^3$ or more than 15,000/mm$^3$; and wherein the act of re-assessing the risk of occurrence of a bacterial infection in the febrile infant based on the laboratory result data in combination with the historical data and the physical examination data comprises an act of determining that the febrile infant is at increased risk for bacterial infection based on the white blood cell count.

54. The method as recited in claim 52, wherein the act accessing one or more of a white blood cell count, a band count, and urinalysis result data comprises an act of accessing a band count that less than 1,500 bands/mm$^3$; and wherein the act of re-assessing the risk of occurrence of a bacterial infection in the febrile infant based on the laboratory result data in combination with the historical data and the physical examination data comprises further comprises an act of determining that the febrile infant is at increased risk for bacterial infection based on the band count.

55. The method as recited in claim 52, wherein the act accessing one or more of a white blood cell count, a band count, and urinalysis result data comprises an act of accessing urinalysis result data indicative of more than 10 white blood cells/hpf; and wherein the act of re-assessing the risk of occurrence of a bacterial infection in the febrile infant based on the laboratory result data in combination with the historical data and the physical examination data comprises further comprises an act of determining that the febrile infant is at increased risk for bacterial infection based on urinalysis result data.

56. The method as recited in claim 49, wherein the act of accessing viral diagnostic test result data corresponding to the febrile infant subsequent to accessing the Rochester criteria data including the laboratory result data comprises an act of accessing viral diagnostic test result data indicative of the febrile infant having a viral infection.

57. The method as recited in claim 56, wherein the act of accessing viral diagnostic test result data indicative of the febrile infant having a viral infection comprises an act of accessing viral diagnostic data indicative of the febrile infant being infected with a virus selected from among RSV, Influenza A, Influenza B, parainfluenza 1, parainfluenza 2, parainfluenza 3, adenovirus, HHV 6, and rhinovirus.

58. The method as recited in claim 56, wherein the act of re-assessing the risk of occurrence of a bacterial infection in the febrile infant based on the viral diagnostic test result data in combination with the laboratory result data, the historical data, and the physical examination data comprises an act of determining that the febrile infant is at reduced risk for bacterial infection based on the viral diagnostic test result data indicating that the febrile infant has a viral infection.

59. A computer program product for use in a computing environment having a database associated therewith, the computer program product for implementing a method for refining an assessment of risk for bacterial infection in a febrile infant as medical information for the febrile infant becomes available, the computer program product comprising one or more computer-readable media have stored thereon computer-executable instructions that, when executed at a processor, cause the computing environment to perform the method including the following:

access Rochester criteria data including historical data and physical examination data corresponding to a febrile infant;

assess a risk of occurrence of a bacterial infection in the febrile infant based on the historical data and physical examination data;

access Rochester criteria data including laboratory result data corresponding to the febrile infant subsequent to accessing the Rochester criteria data including the historical data and the physical examination data;

re-assess the risk of occurrence of a bacterial infection in the febrile infant based on the laboratory result data in combination with the historical data and the physical examination data;

access viral diagnostic test result data corresponding to the febrile infant subsequent to accessing the Rochester criteria data including the laboratory result data;

re-assess the risk of occurrence of a bacterial infection in the febrile infant based on the viral diagnostic test result data in combination with the laboratory result data, the historical data, and the physical examination data;

access bacterial culture result data corresponding to the febrile infant subsequent to accessing the viral diagnostic test result data; and re-assess the risk of occurrence of a bacterial infection in the febrile infant based on the bacterial culture result data in combination with the viral diagnostic result data, the laboratory result data, the historical data, and the physical examination data.

* * * * *

UNITED STATES PATENT AND TRADEMARK OFFICE
CERTIFICATE OF CORRECTION

PATENT NO. : 7,461,046 B2  Page 1 of 1
APPLICATION NO. : 10/503033
DATED : December 2, 2008
INVENTOR(S) : Byington et al.

It is certified that error appears in the above-identified patent and that said Letters Patent is hereby corrected as shown below:

Title Page, insert:
--(60) Related U.S. Application Data
Provisional application No. 60/355,001, filed on 02/07/2002--.

Signed and Sealed this

Twentieth Day of July, 2010

David J. Kappos
*Director of the United States Patent and Trademark Office*